US010300332B2

(12) United States Patent
Ito et al.

(10) Patent No.: US 10,300,332 B2
(45) Date of Patent: May 28, 2019

(54) ELECTRONIC APPARATUS, SYSTEM, PRESENTATION METHOD, PRESENTATION PROGRAM, AND RECORDING MEDIUM

(71) Applicant: SEIKO EPSON CORPORATION, Tokyo (JP)

(72) Inventors: Tsuyoshi Ito, Suwa (JP); Kenya Kodaira, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 195 days.

(21) Appl. No.: 15/387,093

(22) Filed: Dec. 21, 2016

(65) Prior Publication Data

US 2017/0203151 A1 Jul. 20, 2017

(30) Foreign Application Priority Data

Jan. 15, 2016 (JP) .................... 2016-005804

(51) Int. Cl.
| | |
|---|---|
| *A61B 5/11* | (2006.01) |
| *G06K 9/00* | (2006.01) |
| *A63B 24/00* | (2006.01) |
| *A63B 69/36* | (2006.01) |
| *A63B 71/06* | (2006.01) |

(52) U.S. Cl.
CPC ............ *A63B 24/0003* (2013.01); *A61B 5/11* (2013.01); *A63B 69/36* (2013.01); *A63B 71/0619* (2013.01); *G06K 9/00342* (2013.01); *A63B 2071/0663* (2013.01); *A63B 2071/0666* (2013.01); *A63B 2220/34* (2013.01); *A63B 2220/40* (2013.01)

(58) Field of Classification Search
CPC . A63B 69/36; A63B 2220/40; A63B 24/0003; A63B 24/0006; A63B 69/3632; A63B 2220/803; A63B 2220/833; A63B 71/0619; A63B 2225/50; A61B 5/6895; A61B 5/11; A61B 2503/10; A61B 2562/0219; G09B 19/0038; G06K 9/00342
See application file for complete search history.

(56) References Cited

U.S. PATENT DOCUMENTS

| | | | | |
|---|---|---|---|---|
| 9,173,596 | B1* | 11/2015 | Berme ................ | G06F 19/3481 |
| 9,717,969 | B2* | 8/2017 | Sato ................... | G09B 19/0038 |
| 9,864,904 | B2* | 1/2018 | Saiki ................. | G06K 9/00342 |
| 9,962,591 | B2* | 5/2018 | Sato ................... | A63B 69/3632 |
| 9,999,394 | B2* | 6/2018 | Shibuya .................. | A61B 5/11 |
| 2004/0096085 | A1* | 5/2004 | Matsumoto ........ | A63B 24/0003 382/107 |
| 2006/0052173 | A1* | 3/2006 | Telford ............. | A63B 24/0003 473/131 |

(Continued)

FOREIGN PATENT DOCUMENTS

| | | |
|---|---|---|
| JP | 2014-100341 A | 6/2014 |
| JP | 2015-002910 A | 1/2015 |

*Primary Examiner* — William H McCulloch, Jr.
(74) *Attorney, Agent, or Firm* — Oliff PLC

(57) ABSTRACT

An electronic apparatus includes a processor that calculates identification data indicating a region in which a ball hitting portion of an exercise appliance is included at each of a plurality of timings during a swing of the exercise appliance, of a plurality of regions to which the identification data is allocated in advance, and displays the identification data to a user.

28 Claims, 29 Drawing Sheets

(56) References Cited

U.S. PATENT DOCUMENTS

| | | | | |
|---|---|---|---|---|
| 2006/0252541 | A1* | 11/2006 | Zalewski | A63F 13/02 463/36 |
| 2011/0190052 | A1* | 8/2011 | Takeda | A63F 13/02 463/31 |
| 2012/0128203 | A1* | 5/2012 | Nakaoka | A63B 69/36 382/103 |
| 2014/0073446 | A1* | 3/2014 | Davenport | A63B 24/0006 473/223 |
| 2014/0200094 | A1* | 7/2014 | Parke | A63F 13/00 473/223 |
| 2014/0228141 | A1 | 8/2014 | Sakyo et al. | |
| 2014/0379293 | A1* | 12/2014 | Sato | G09B 19/003 702/141 |
| 2014/0379295 | A1* | 12/2014 | Sato | G09B 19/003 702/142 |
| 2015/0072797 | A1* | 3/2015 | Sakyo | A63B 24/0006 473/223 |
| 2015/0196823 | A1 | 7/2015 | Sato | |
| 2015/0283428 | A1* | 10/2015 | Shibuya | G01P 13/00 473/221 |
| 2015/0285834 | A1* | 10/2015 | Shibuya | G01P 15/0802 702/150 |
| 2015/0367174 | A1* | 12/2015 | Okazaki | A63B 24/0003 473/409 |
| 2017/0011652 | A1* | 1/2017 | Kodaira | G09B 19/0038 |
| 2017/0028251 | A1* | 2/2017 | Ito | G09B 19/0038 |
| 2017/0028253 | A1* | 2/2017 | Hagiwara | G06K 9/00342 |
| 2017/0028254 | A1* | 2/2017 | Ito | A63B 69/36 |
| 2017/0028282 | A1* | 2/2017 | Ito | A63B 60/46 |
| 2017/0028283 | A1* | 2/2017 | Ito | A61B 5/6895 |
| 2017/0203151 | A1* | 7/2017 | Ito | A63B 24/0003 |
| 2017/0203172 | A1* | 7/2017 | Ito | A63B 69/36 |
| 2017/0203186 | A1* | 7/2017 | Sato | G06F 17/30336 |
| 2017/0203211 | A1* | 7/2017 | Kiryu | A63F 13/211 |
| 2017/0215771 | A1* | 8/2017 | Sayo | A63B 69/36 |
| 2017/0296869 | A1* | 10/2017 | Kiryu | A63B 71/0622 |
| 2017/0296870 | A1* | 10/2017 | Kiryu | G06T 7/20 |

\* cited by examiner

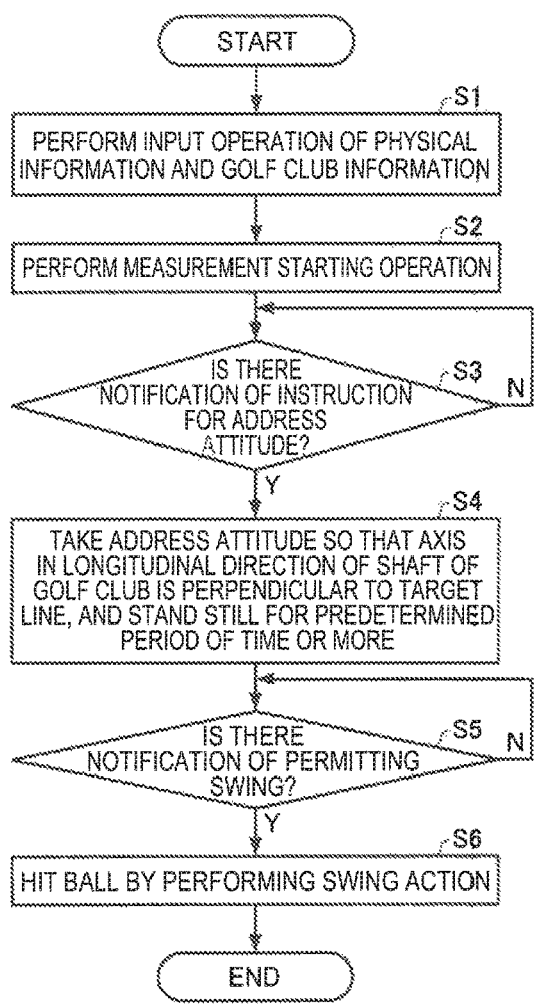

| DATE AND TIME | GOLF CLUB | HEAD SPEED | FACE ANGLE | CLUB PATH (INCIDENCE ANGLE) | SHAFT AXIS ROTATION (TOP) | GRIP DECELERATION RATIO | GRIP DECELERATION TIME RATIO |
|---|---|---|---|---|---|---|---|
| ☑ 2015/07/01 00:01:00 PM | 1W | 40.0 m/s | 4.0 deg | -1.0 deg | 70.0 deg | 30.0 % | 14.0 % |
| ☐ 2015/07/01 00:59:00 PM | 1W | 39.0 m/s | 3.9 deg | -0.9 deg | 69.0 deg | 29.0 % | 13.0 % |
| ☐ 2015/07/01 00:58:00 PM | 1W | 41.0 m/s | 4.1 deg | -1.1 deg | 71.0 deg | 31.0 % | 15.0 % |
| ☐ 2015/07/01 00:57:00 PM | 7I | 38.0 m/s | 3.8 deg | -0.8 deg | 68.0 deg | 28.0 % | 12.0 % |
| ☐ 2015/07/01 00:56:00 PM | 7I | 37.0 m/s | 3.7 deg | -0.7 deg | 67.0 deg | 27.0 % | 11.0 % |

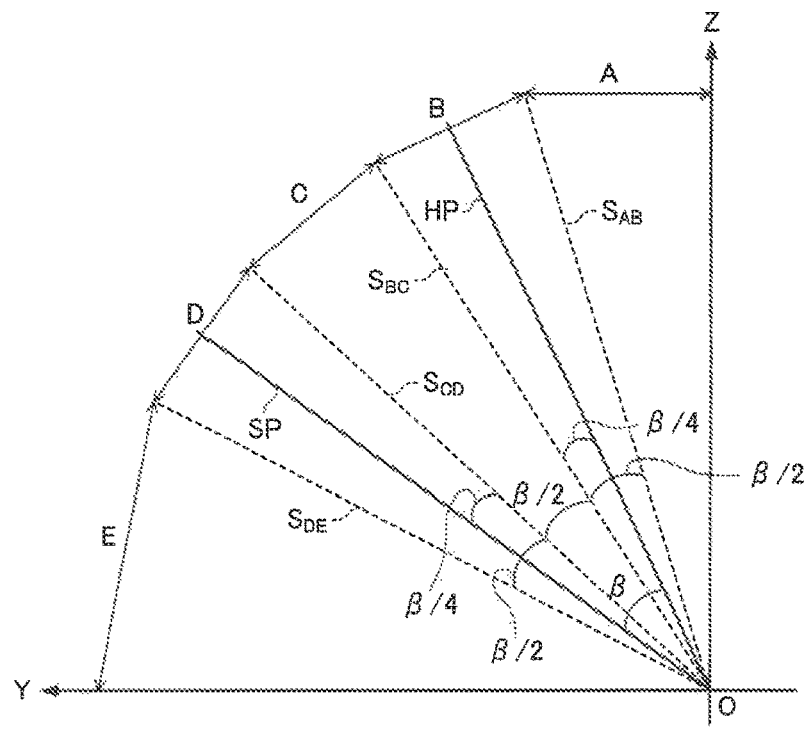
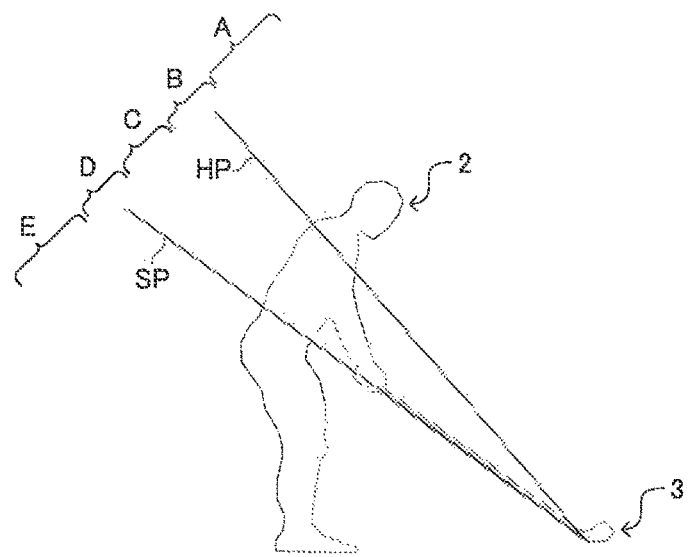
FIG. 20

| POSITIONAL RELATIONSHIP OF V ZONE | | | | SCORE | SWING TYPE (DIAGNOSIS INFORMATION) |
|---|---|---|---|---|---|
| HALFWAY BACK | TOP | NATURAL UNCOCK POINT | HALFWAY DOWN | | |
| A | A | A | A | PV1 | LV1 |
| A | A | A | B | | |
| A | A | A | C | PV2 | |
| A | A | A | D | | |
| A | A | A | E | | LV2 |
| A | A | B | A | PV3 | |
| . | . | . | . | | |
| . | . | . | . | PV4 | LV3 |
| . | . | . | . | | |
| . | . | . | . | PV5 | |
| . | . | . | . | | . |
| . | . | . | . | | . |
| B | B | B | B | | |
| B | B | B | A | | |
| B | B | B | C | | |
| B | B | B | D | | |
| . | . | . | . | | |
| C | C | C | C | | |
| . | . | . | . | | |
| D | D | D | D | | |
| . | . | . | . | | LVm |
| E | E | E | E | PVn | |

FIG. 25

ELECTRONIC APPARATUS, SYSTEM, PRESENTATION METHOD, PRESENTATION PROGRAM, AND RECORDING MEDIUM

BACKGROUND

1. Technical Field

The present invention relates to an electronic apparatus, a system, a presentation method, a presentation program, and a recording medium.

2. Related Art

JP-A-2014-100341 discloses a motion analysis system which performs swing analysis by using a motion sensor, and displays a processing result as text, graphs, and other images.

However, JP-A-2014-100341 does not disclose a specific configuration for notifying a user of the process of a swing. An analysis apparatus which displays a swing trajectory (for example, a trajectory of a head of a golf club) has already been proposed, but it is very hard for a user to objectively understand the user's swing type on the basis of only the trajectory.

SUMMARY

An advantage of some aspects of the invention is to provide an electronic apparatus, a system, a presentation method, a presentation program, and a recording medium, capable of objectively and simply presenting the type of swing to a user.

The term "type of swing" mentioned in the present specification indicates a swing type which is classified depending on the manner of a swing transitioning (a temporal change pattern of a swing).

The invention can be implemented as the following forms or application examples.

APPLICATION EXAMPLE 1

An electronic apparatus according to this application example includes a presentation unit that presents identification data indicating a region in which a ball hitting portion of an exercise appliance is included at each of a plurality of timings during a swing, of a plurality of regions to which the identification data is allocated in advance, to a user, by using an output from an inertial sensor.

According to the electronic apparatus of this application example, identification data of regions in which the ball hitting portion is included at a plurality of respective timings is presented in a time series (that is, in an order of reaching a plurality of timings), and thus a user can recognize the type of user's swing as an arrangement pattern of the identification data.

APPLICATION EXAMPLE 2

In the application example, the presentation unit may present the identification data to the user in a time series.

APPLICATION EXAMPLE 3

In the electronic apparatus of the application example, the plurality of regions may be set on the basis of a first virtual plane indicating a basic attitude of the exercise appliance.

Therefore, the electronic apparatus of this application example can present the type of swing with a basic attitude of an exercise appliance as a reference.

APPLICATION EXAMPLE 4

In the electronic apparatus of the application example, the first virtual plane may be a plane specified on the basis of a first axis along a target hit ball direction and a second axis along a longitudinal direction of the exercise appliance before a backswing is started.

Therefore, the electronic apparatus of this application example can present the type of swing with a basic attitude of an exercise appliance before a backswing is started and a target hit ball direction as a reference.

APPLICATION EXAMPLE 5

In the electronic apparatus of the application example, the plurality of regions may be set on the basis of the first virtual plane, and a second virtual plane passing through the vicinity of the shoulder of the user.

Therefore, the electronic apparatus of this application example can present the type of swing with a basic attitude of an exercise appliance before a backswing is started, a target hit ball direction, and a user's basic attitude as a reference.

APPLICATION EXAMPLE 6

In the electronic apparatus of the application example, the second virtual plane may be a plane which includes the first axis and forms a predetermined angle with the first virtual plane.

Therefore, the electronic apparatus of this application example can present the type of swing with a zone (V zone) interposed between the first virtual plane and the second virtual plane as a reference.

APPLICATION EXAMPLE 7

In the electronic apparatus of the application example, the second virtual plane may be a plane which is parallel to the first virtual plane.

Therefore, the electronic apparatus of this application example can present the type of swing with a zone (parallel zone) interposed between the first virtual plane and the second virtual plane as a reference.

APPLICATION EXAMPLE 8

In the electronic apparatus of the application example, the presentation unit may present the first virtual plane and the second virtual plane to the user along with the identification data.

Therefore, according to the electronic apparatus of this application example, a user can check a relationship between the type of swing, and the first virtual plane and the second virtual plane.

APPLICATION EXAMPLE 9

In the electronic apparatus of the application example, the presentation unit may present a trajectory of the swing to the user along with the identification data.

Therefore, according to the electronic apparatus of this application example, a user can check a swing trajectory along with the type of swing.

APPLICATION EXAMPLE 10

In the electronic apparatus of the application example, the plurality of timings may include at least two of a timing at which a longitudinal direction of the exercise appliance is along a horizontal plane during a backswing, a timing of a top, a timing at which a holding portion of the exercise appliance starts to decelerate during a downswing, and a timing at which the longitudinal direction of the exercise appliance is along the horizontal plane during the downswing.

Therefore, the electronic apparatus of this application example can reflect attitudes of an exercise appliance at at least two representative timings of a swing in an arrangement of identification data.

APPLICATION EXAMPLE 11

In the electronic apparatus of the application example, the inertial sensor may include at least one of an acceleration sensor and an angular velocity sensor.

Therefore, the electronic apparatus can present identification data, for example, on the basis of at least one of an acceleration, a speed, a position, an attitude change, and an attitude of an exercise appliance.

APPLICATION EXAMPLE 12

In the electronic apparatus of the application example, the presentation unit may present a level on the basis of the presented identification data.

APPLICATION EXAMPLE 13

In the electronic apparatus of the application example, the presentation unit may present diagnosis information on the basis of the presented identification data.

APPLICATION EXAMPLE 14

In the application example, the presentation unit may present information regarding a swing practice method on the basis of the diagnosis information.

APPLICATION EXAMPLE 15

A system according to this application example includes any one of the electronic apparatuses according to the application examples; and the inertial sensor.

APPLICATION EXAMPLE 16

A system according to this application example includes any one of the electronic apparatuses according to the application examples; and a head mounted display device that displays the identification data.

APPLICATION EXAMPLE 17

A system according to this application example includes any one of the electronic apparatuses according to the application examples; and a wrist mounted display device that displays the identification data.

APPLICATION EXAMPLE 18

A presentation method according to this application example includes presenting identification data indicating a region in which a ball hitting portion of an exercise appliance is included at each of a plurality of timings during a swing, of a plurality of regions to which the identification data is allocated, to a user, by using an output from an inertial sensor.

APPLICATION EXAMPLE 19

In the application example, in the presenting of the identification data, the identification data may be presented to the user in a time series.

APPLICATION EXAMPLE 20

In the application example, the plurality of regions may be set on the basis of a first virtual plane indicating a basic attitude of the exercise appliance.

APPLICATION EXAMPLE 21

In the application example, the first virtual plane may be a plane specified on the basis of a first axis along a target hit ball direction and a second axis along a longitudinal direction of the exercise appliance before a backswing is started.

APPLICATION EXAMPLE 22

In the application example, the plurality of regions may be set on the basis of the first virtual plane, and a second virtual plane passing through the vicinity of the shoulder of the user.

APPLICATION EXAMPLE 23

In the application example, the second virtual plane may be a plane which includes the first axis and forms a predetermined angle with the first virtual plane.

APPLICATION EXAMPLE 24

In the application example, the second virtual plane may be a plane which is parallel to the first virtual plane.

APPLICATION EXAMPLE 25

In the application example, in the presenting of the identification data, the first virtual plane and the second virtual plane may be presented to the user along with the identification data.

APPLICATION EXAMPLE 26

In the application example, in the presenting of the identification data, a trajectory of the swing may be presented to the user along with the identification data.

APPLICATION EXAMPLE 27

In the application example, the plurality of timings may include at least two of a timing at which a longitudinal direction of the exercise appliance is along a horizontal plane during a backswing, a timing of a top, a timing at which a holding portion of the exercise appliance starts to decelerate during a downswing, and a timing at which the longitudinal direction of the exercise appliance is along the horizontal plane during the downswing.

APPLICATION EXAMPLE 28

A presentation program according to this application example causes a computer to execute presenting identification data indicating a region in which a ball hitting portion of an exercise appliance is included at each of a plurality of timings during a swing, of a plurality of regions to which the identification data is allocated in advance, to a user, by using an output from an inertial sensor.

APPLICATION EXAMPLE 29

A recording medium according to this application example records a presentation program causing a computer to execute presenting identification data indicating a region in which a ball hitting portion of an exercise appliance is included at each of a plurality of timings during a swing, of a plurality of regions to which the identification data is allocated in advance, to a user, by using an output from an inertial sensor.

BRIEF DESCRIPTION OF THE DRAWINGS

The invention will be described with reference to the accompanying drawings, wherein like numbers reference like elements.

FIG. 4 is a diagram illustrating procedures of actions performed by a user until the user hits a ball.

FIG. 5 is a diagram illustrating an example of an input screen of physical information and golf club information.

FIG. 7 is a diagram illustrating an example of a selection screen of swing analysis data.

FIG. 20 is a diagram illustrating examples of relationships among the shaft plane and the Hogan plane, and a plurality of regions A, B, C, D and E.

FIG. 25 is a diagram illustrating an example of a V zone correspondence table.

DESCRIPTION OF EXEMPLARY EMBODIMENTS

Hereinafter, preferred embodiments of the invention will be described with reference to the drawings. The embodiments described below are not intended to improperly limit the content of the invention disclosed in the appended claims. In addition, all constituent elements described below are not essential constituent elements of the invention.

Hereinafter, a swing analysis system analyzing a golf swing will be described as an example.

1. Swing Analysis System 1-1. Configuration of Swing Analysis System

Figure 1:
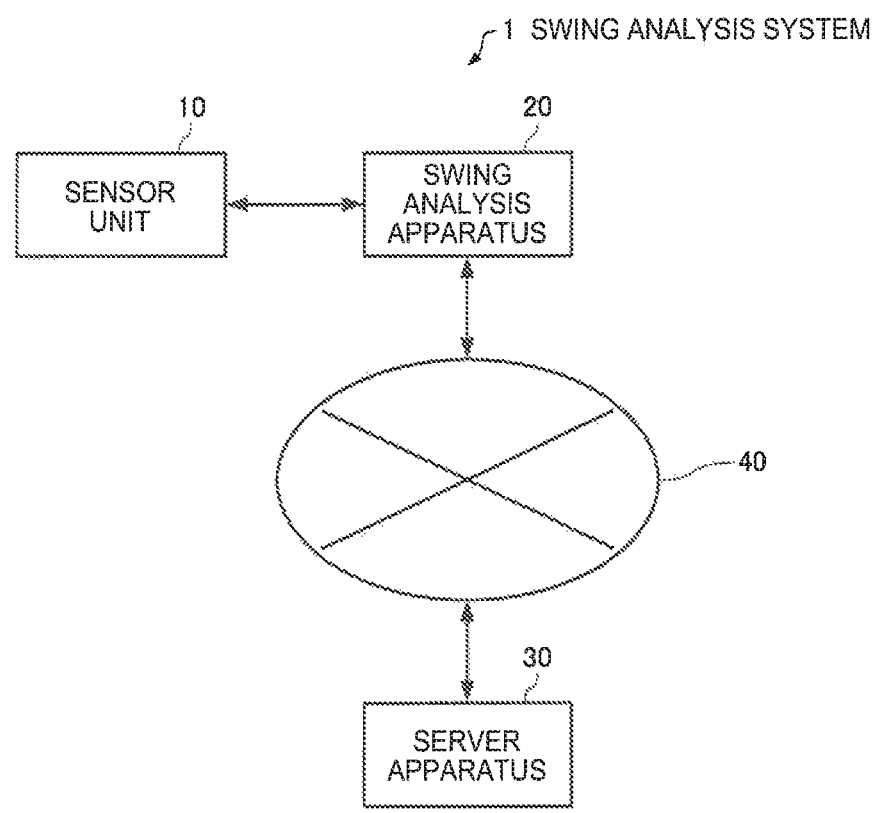
FIG. 1 is a diagram illustrating a configuration example of a swing analysis system of the present embodiment.

FIG. 1 is a diagram illustrating a configuration example of a swing analysis system of the present embodiment. As illustrated in FIG. 1, a swing analysis system 1 of the present embodiment is configured to include a sensor unit 10, a swing analysis apparatus 20, and a server apparatus 30.

Figure 2:
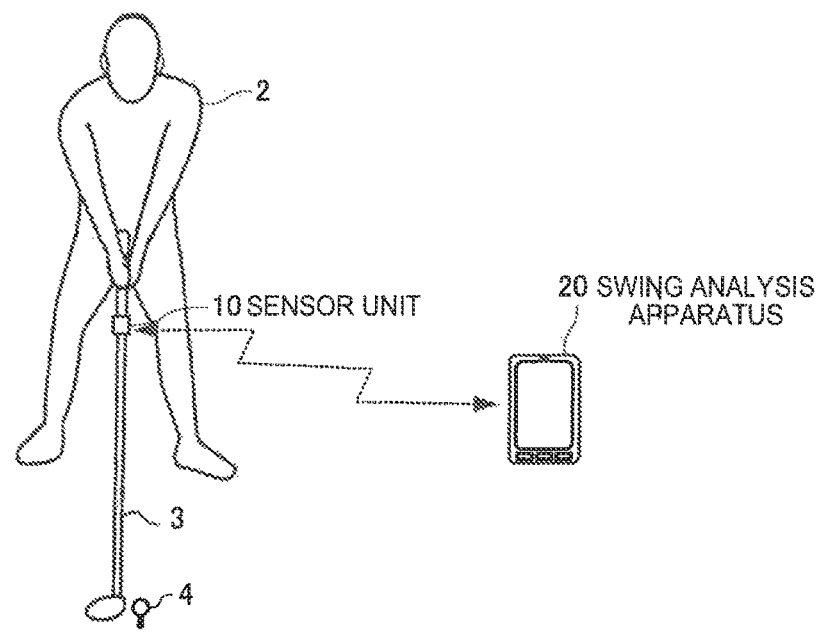
FIG. 2 is a diagram illustrating an example in which a sensor unit is attached.

The sensor unit 10 (an example of an inertial sensor) can measure acceleration generated in each axial direction of three axes and angular velocity generated around each of the three axes, and is attached to a golf club 3 as illustrated in FIG. 2.

Figure 3:
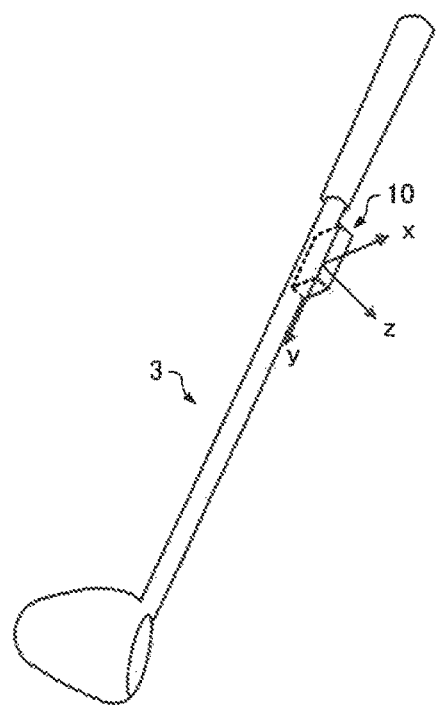
FIG. 3 is a diagram illustrating examples of a position at which and a direction in which the sensor unit is attached.

In the present embodiment, as illustrated in FIG. 3, the sensor unit 10 is attached to a part of a shaft so that one axis of three detection axes (an x axis, a y axis, and a z axis), for example, the y axis matches a longitudinal direction of the shaft of the golf club 3 (a longitudinal direction of the golf club 3; hereinafter, referred to as a longitudinal direction). Preferably, the sensor unit 10 is attached to a position close to a grip (an example of a holding portion) to which impact during ball hitting is hardly forwarded and a centrifugal force is not applied during a swing. The shaft is a shaft portion other than a head of the golf club 3 and also includes the grip. However, the sensor unit 10 may be attached to a part (for example, the hand or a glove) of a user 2, and may be attached to an accessory such as a wristwatch.

The user 2 performs a swing action for hitting a golf ball 4 according to predefined procedures. FIG. 4 is a diagram illustrating procedures of actions performed by the user 2 before and until the user hits the ball. As illustrated in FIG. 4, first, the user 2 performs an input operation of physical information of the user 2, information (golf club information) regarding the golf club 3 used by the user 2, and the like via the swing analysis apparatus 20 (step S1). The physical information may include at least one of information regarding a height of the user, a length of the arms of the user, and a length of the legs of the user 2, and may further include information regarding sex or other information. The golf club information includes at least one of information regarding a length (club length) of the golf club 3 and the type (number) of golf club 3. Next, the user 2 performs a measurement starting operation (an operation for starting measurement in the sensor unit 10) via the swing analysis apparatus 20 (step S2). Next, after receiving a notification (for example, a notification using a voice) of giving an instruction for taking an address attitude (a basic attitude before starting a swing) from the swing analysis apparatus 20 (Y in step S3), the user 2 takes an address attitude so that the axis in the longitudinal direction of the shaft of the golf club 3 is perpendicular to a target line (target hit ball direction), and stands still (step S4). Next, the user 2 receives a notification (for example, a notification using a voice) of permitting a swing from the swing analysis apparatus 20 (Yin step S5), and then the user hits the golf ball 4 by performing a swing action (step S6).

An attitude of an exercise appliance when the user 2 takes an address attitude is a basic attitude of the exercise appliance. An attitude of the exercise appliance before the user 2 starts a swing may be a basic attitude of the exercise appliance.

FIG. 5 is a diagram illustrating an example of an input screen of physical information and golf club information, displayed on a display section 25 (refer to FIG. 9) of the swing analysis apparatus 20. In step S1 in FIG. 4, the user 2 inputs physical information such as a height, sex, age, and country, and inputs golf club information such as a club length (a length of the shaft), and a club number on the input screen illustrated in FIG. 5. Information included in the physical information is not limited thereto, and, the physical information may include, for example, at least one of information regarding a length of the arms and a length of the legs of the user instead of or along with the height. Similarly, information included in the golf club information is not limited thereto, and, for example, the golf club information may not include at least one of information regarding the club length and the club number, and may include other information.

If the user 2 performs the measurement starting operation in step S2 in FIG. 4, the swing analysis apparatus 20 transmits a measurement starting command to the sensor unit 10, and the sensor unit 10 receives the measurement starting command and starts measurement of three-axis accelerations and three-axis angular velocities. The sensor unit 10 measures three-axis accelerations and three-axis angular velocities in a predetermined cycle (for example, 1 ms), and sequentially transmits the measured data to the swing analysis apparatus 20. Communication between the sensor unit 10 and the swing analysis apparatus 20 may be wireless communication, and may be wired communication.

The swing analysis apparatus 20 notifies the user 2 of permission of swing starting, shown in step S5 in FIG. 4, and then analyzes the swing action (step S6 in FIG. 4) in which the user 2 has hit the ball by using the golf club 3 on the basis of measured data from the sensor unit 10.

Figure 6:
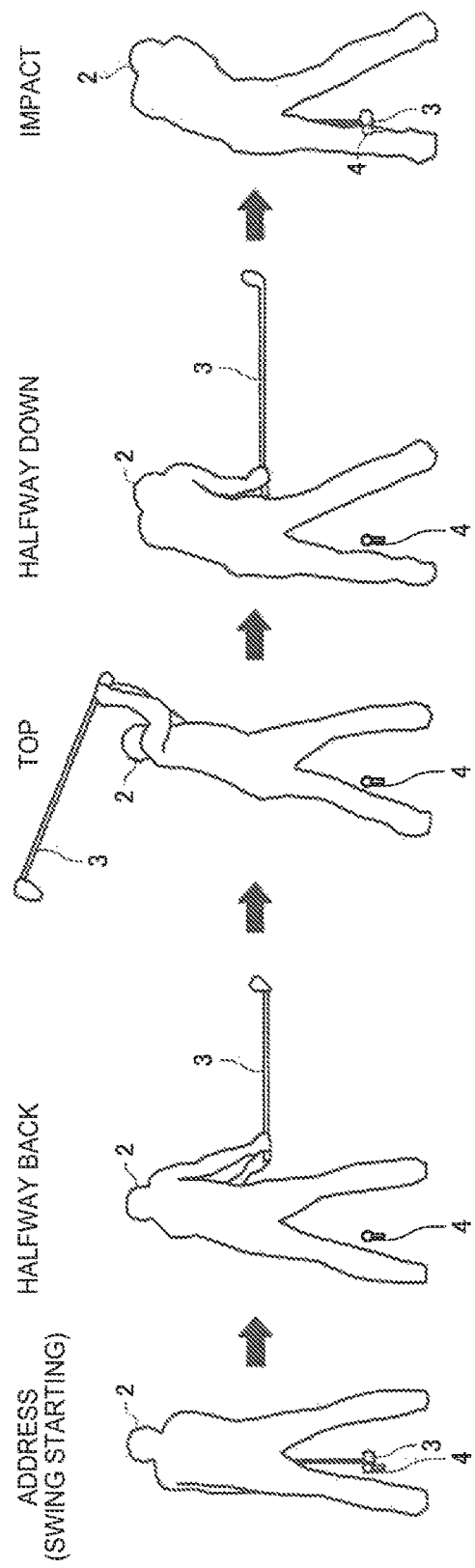
FIG. 6 is a diagram illustrating a swing action.

As illustrated in FIG. 6, the swing action performed by the user 2 in step S6 in FIG. 4 includes an action reaching impact (ball hitting) at which the golf ball 4 is hit through respective states of halfway back at which the shaft of the golf club 3 becomes horizontal during a backswing after starting a swing (backswing), a top at which the swing changes from the backswing to a downswing, and halfway down at which the shaft of the golf club 3 becomes horizontal during the downswing. The swing analysis apparatus 20 generates swing analysis data including information regarding a time point (date and time) at which the swing is performed, identification information or the sex of the user 2, the type of golf club 3, and an analysis result of the swing action, and transmits the swing analysis data to the server apparatus 30 via a network 40 (refer to FIG. 1).

The server apparatus 30 receives the swing analysis data transmitted by the swing analysis apparatus 20 via the network 40, and preserves the swing analysis data. Therefore, when the user 2 performs a swing action according to the procedures illustrated in FIG. 4, the swing analysis data generated by the swing analysis apparatus 20 is preserved in the server apparatus 30, and thus a swing analysis data list is built.

For example, the swing analysis apparatus 20 is implemented by an information terminal (client terminal) such as a smart phone or a personal computer, and the server apparatus 30 is implemented by a server which processes requests from the swing analysis apparatus 20.

The network 40 may be a wide area network (WAN) such as the Internet, and may be a local area network (LAN). Alternatively, the swing analysis apparatus 20 and the server apparatus 30 may communicate with each other through, for example, near field communication or wired communication, without using the network 40.

In the present embodiment, if the user 2 activates a swing diagnosis application via an operation section 23 (refer to FIG. 9) of the swing analysis apparatus 20, the swing analysis apparatus 20 performs communication with the server apparatus 30, and, for example, a selection screen of swing analysis data as illustrated in FIG. 7 is displayed on the display section 25 of the swing analysis apparatus 20. The selection screen includes a time point (date and time), the type of golf club which has been used, and some index values as analysis results of a swing, with respect to each item of swing analysis data regarding the user 2 included in the swing analysis data list preserved in the server apparatus 30.

Figure 8:
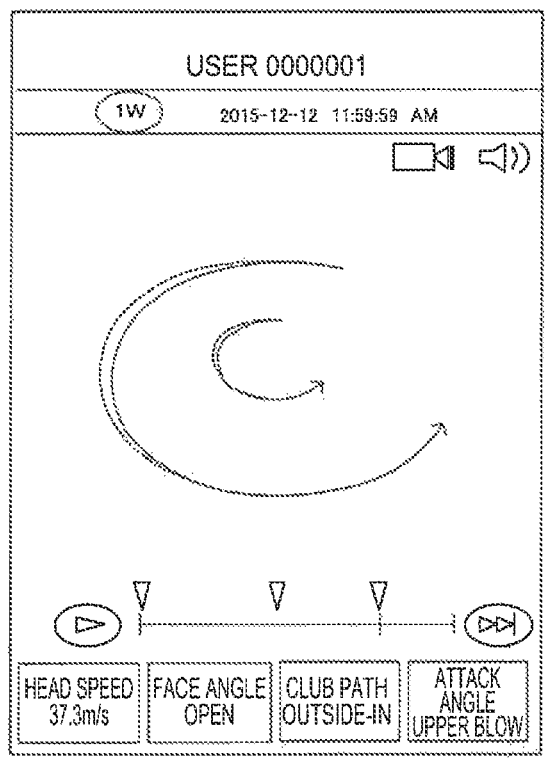
FIG. 8 is a diagram illustrating an example of a display screen.

A checkbox correlated with each item of swing analysis data is located at a left end of the selection screen illustrated in FIG. 7, and the user 2 checks any one of the checkboxes by operating the swing analysis apparatus 20, and then presses an OK button located on a lower part in the selection screen. Consequently, the swing analysis apparatus 20 performs communication with the server apparatus 30, and displays swing analysis data correlated with the checked checkbox on the selection screen illustrated in FIG. 7, on the display section 25 of the swing analysis apparatus 20 (for example, refer to FIG. 8).

1-2. Configurations of Sensor Unit and Swing Analysis Apparatus

Figure 9:
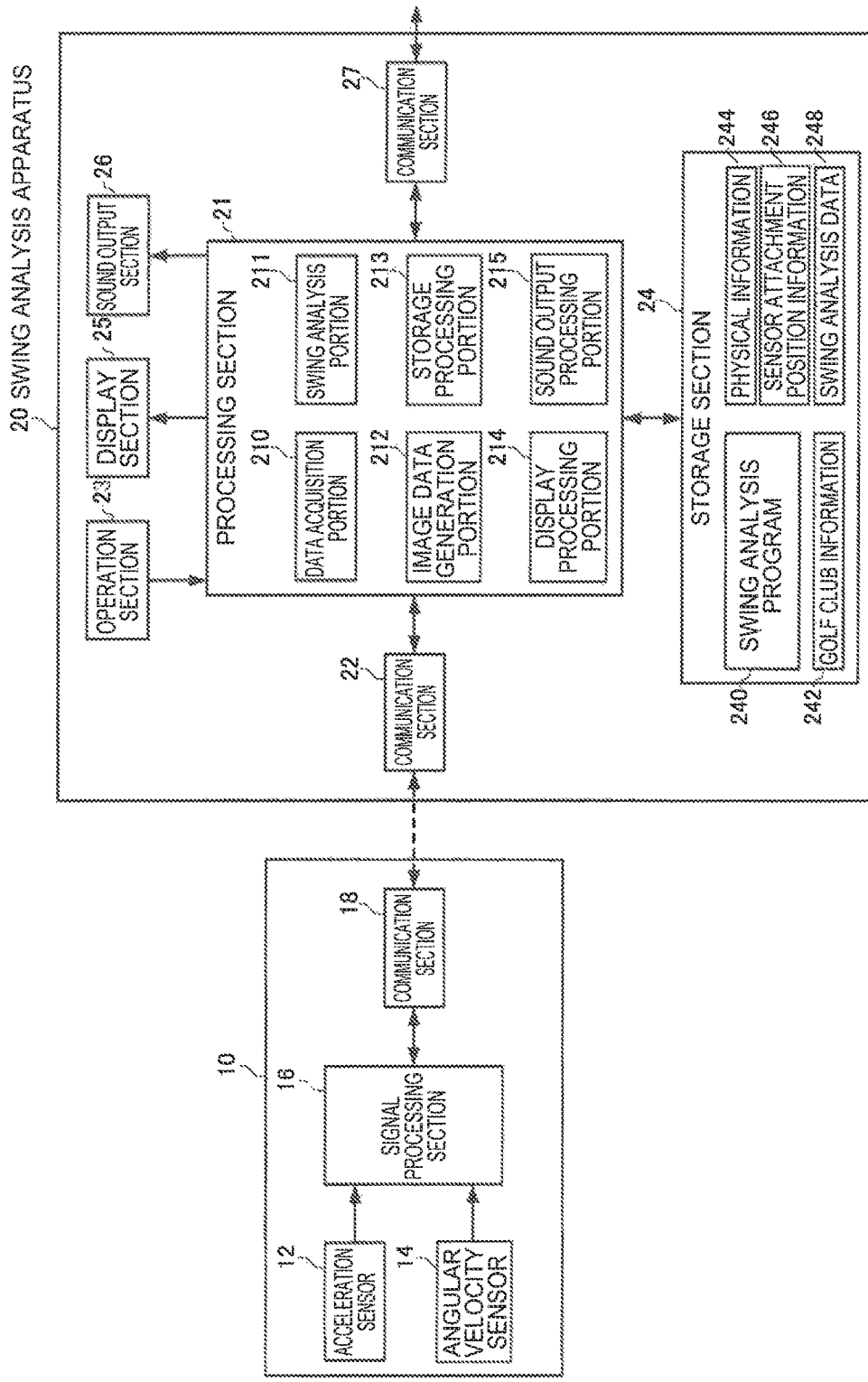
FIG. 9 is a diagram illustrating configuration examples of the sensor unit and a swing analysis apparatus.

FIG. 9 is a diagram illustrating configuration examples of the sensor unit 10 and the swing analysis apparatus 20. As illustrated in FIG. 9, in the present embodiment, the sensor unit 10 is configured to include an acceleration sensor 12, an angular velocity sensor 14, a signal processing section 16, and a communication section 18. However, the sensor unit 10 may have a configuration in which some of the constituent elements are deleted or changed as appropriate, or may have a configuration in which other constituent elements are added thereto.

The acceleration sensor 12 measures respective accelerations in three axial directions which intersect (ideally, orthogonal to) each other, and outputs digital signals (acceleration data) corresponding to magnitudes and directions of the measured three-axis accelerations.

The angular velocity sensor 14 measures respective angular velocities in three axial directions which intersect (ideally, orthogonal to) each other, and outputs digital signals (angular velocity data) corresponding to magnitudes and directions of the measured three-axis angular velocities.

The signal processing section 16 receives the acceleration data and the angular velocity data from the acceleration sensor 12 and the angular velocity sensor 14, respectively, adds time information thereto, stores the data in a storage portion (not illustrated), adds time information to the stored measured data (an example of acceleration data and angular velocity data) so as to generate packet data conforming to a communication format, and outputs the packet data to the communication section 18. The signal processing section 16 is constituted of a processing device such as a CPU or other processor.

Ideally, the acceleration sensor 12 and the angular velocity sensor 14 are provided in the sensor unit 10 so that the three axes thereof match three axes (an x axis, a y axis, and a z axis) of an orthogonal coordinate system (sensor coordinate system) defined for the sensor unit 10, but, actually, errors occur in installation angles. Therefore, the signal processing section 16 performs a process of converting the acceleration data and the angular velocity data into data in the xyz coordinate system by using a correction parameter which is calculated in advance according to the installation angle errors.

The signal processing section 16 may perform a process of correcting the temperatures of the acceleration sensor 12 and the angular velocity sensor 14. Alternatively, the acceleration sensor 12 and the angular velocity sensor 14 may have a temperature correction function.

The acceleration sensor 12 and the angular velocity sensor 14 may output analog signals, and, in this case, the signal processing section 16 may A/D convert an output signal from the acceleration sensor 12 and an output signal from the angular velocity sensor 14 so as to generate measured data (acceleration data and angular velocity data), and may generate communication packet data by using the data.

The communication section 18 performs a process of transmitting packet data received from the signal processing section 16 to the swing analysis apparatus 20, or a process of receiving a control command such as a measurement starting command from the swing analysis apparatus 20 and sending the control command to the signal processing section 16. The signal processing section 16 performs various processes corresponding to control commands.

As illustrated in FIG. 9, in the present embodiment, the swing analysis apparatus 20 is configured to include a processing section 21, a communication section 22, an operation section 23, a storage section 24, a display section 25, a sound output section 26, and a communication section 27. However, the swing analysis apparatus 20 may have a configuration in which some of the constituent elements are deleted or changed as appropriate, or may have a configuration in which other constituent elements are added thereto.

The communication section 22 performs a process of receiving packet data transmitted from the sensor unit 10 and sending the packet data to the processing section 21, or a process of transmitting a control command from the processing section 21 to the sensor unit 10. The processing section 21 is constituted of a processing device such as a CPU or other processor.

The operation section 23 performs a process of acquiring operation data from the user 2 and sending the operation data to the processing section 21. The operation section 23 may be, for example, a touch panel type display, a button, a key, or a microphone.

The storage section 24 is constituted of, for example, various IC memories such as a read only memory (ROM), a flash ROM, and a random access memory (RAM), or a recording medium such as a hard disk or a memory card. The storage section 24 stores a program for the processing section 21 performing various calculation processes or a control process, or various programs or data for realizing application functions.

In the present embodiment, the storage section 24 stores a swing analysis program 240 which is read by the processing section 21 and executes a swing analysis process. The swing analysis program 240 may be stored in a nonvolatile recording medium (computer readable recording medium) in advance, or the swing analysis program 240 may be received from a server (not illustrated) or the server apparatus 30 by the processing section 21 via a network, and may be stored in the storage section 24.

In the present embodiment, the storage section 24 stores golf club information 242, physical information 244, sensor attachment position information 246, and swing analysis data 248. For example, the user 2 may operate the operation section 23 so as to input specification information regarding the golf club 3 (for example, at least some information such as information regarding a length of the shaft, a position of the centroid thereof, a lie angle, a face age, a loft angle, and the like) from the input screen illustrated in FIG. 5, and the input specification information may be used as the golf club information 242. Alternatively, in step S1 in FIG. 4, the user 2 may sequentially input type numbers of the golf club 3 (alternatively, selects a type number from a type number list) so that specification information for each type number is stored in the storage section 24 in advance. In this case, specification information of an input type number may be used as the golf club information 242.

For example, the user 2 may input physical information by operating the operation section 23 from the input screen illustrated in FIG. 5, and the input physical information may be used as the physical information 244. For example, in step S1 in FIG. 4, the user 2 may input an attachment position of the sensor unit 10 and a distance to the grip of the golf club 3 by operating the operation section 23, and the input distance information may be used as the sensor attachment position information 246. Alternatively, the sensor unit 10 may be attached at a defined predetermined position (for example, a distance of 20 cm from the grip), and thus information regarding the predetermined position may be stored as the sensor attachment position information 246 in advance.

The swing analysis data 248 is data including information regarding a swing action analysis result in the processing section 21 (swing analysis portion 211) along with a time point (date and time) at which a swing was performed, identification information or the sex of the user 2, and the type of golf club 3.

The storage section 24 is used as a work area of the processing section 21, and temporarily stores data which is input from the operation section 23, results of calculation executed by the processing section 21 according to various programs, and the like. The storage section 24 may store data which is required to be preserved for a long period of time among data items generated through processing of the processing section 21.

The display section 25 displays a processing result in the processing section 21 as text, a graph, a table, animation, and other images. The display section 25 may be, for example, a CRT, an LCD, a touch panel type display, and a head mounted display (HMD). A single touch panel type display may realize functions of the operation section 23 and the display section 25.

The sound output section 26 displays a processing result in the processing section 21 as a sound such as a voice or a buzzer sound. The sound output section 26 may be, for example, a speaker or a buzzer.

The communication section 27 performs data communication with a communication section 32 (refer to FIG. 22) of the server apparatus 30 via the network 40. For example, the communication section 27 performs a process of receiving the swing analysis data 248 from the processing section 21 after a swing analysis process is completed, and transmitting the swing analysis data to the communication section 32 of the server apparatus 30. For example, the communication section 27 performs a process of receiving information required to display the selection screen illustrated in FIG. 7 from the communication section 32 of the server apparatus 30 and transmitting the information to the processing section 21, and a process of receiving selected information on the selection screen illustrated in FIG. 7 from the processing section 21 and transmitting the selected information to the communication section 32 of the server apparatus 30. For example, the communication section 27 performs a process of receiving information required to display the display screen illustrated in FIG. 8 from the communication section 32 of the server apparatus 30, and transmitting the information to the processing section 21.

The processing section 21 performs a process of transmitting a control command to the sensor unit 10 via the communication section 22, or various computation processes on data which is received from the sensor unit 10 via the communication section 22, according to various programs. The processing section 21 performs a process of reading the swing analysis data 248 from the storage section 24, and transmitting the swing analysis data to the server apparatus 30 via the communication section 27, according to various programs. The processing section 21 performs a process of transmitting various pieces of information to the server apparatus 30 via the communication section 27, and displaying various screens (the respective screens illustrated in FIGS. 7 and 8) on the basis of the information received from the server apparatus 30, according to various programs. The processing section 21 performs other various control processes.

Particularly, in the present embodiment, by executing the swing analysis program 240, the processing section 21 functions as a data acquisition portion 210, a swing analysis portion 211, an image data generation portion 212, a storage processing portion 213, a display processing portion 214, and a sound output processing portion 215, and performs a process (swing analysis process) of analyzing a swing action of the user 2.

The data acquisition portion 210 performs a process of receiving packet data which is received from the sensor unit 10 by the communication section 22, acquiring time information and measured data in the sensor unit 10 from the received packet data, and sending the time information and the measured data to the storage processing portion 213. The data acquisition portion 210 performs a process of receiving the information required to display the various screens (the respective screens illustrated in FIGS. 7 and 8), received from the server apparatus 30 by the communication section 27, and transmitting the information to the image data generation portion 212.

The storage processing portion 213 performs read/write processes of various programs or various data for the storage section 24. The storage processing portion 213 performs not only the process of storing the time information and the measured data received from the data acquisition portion 210 in the storage section 24 in correlation with each other, but also a process of storing various pieces of information calculated by the swing analysis portion 211, the swing analysis data 248, or the like in the storage section 24.

The swing analysis portion 211 performs a process of analyzing a swing action of the user 2 by using the measured data (the measured data stored in the storage section 24) output from the sensor unit 10, the data from the operation section 23, or the like, so as to generate the swing analysis data 248 including a time point (date and time) at which the swing was performed, identification information or the sex of the user 2, the type of golf club 3, and information regarding a swing action analysis result. Particularly, in the present embodiment, the swing analysis portion 211 calculates a value of each index of the swing as at least some of the information regarding the swing action analysis result.

The swing analysis portion 211 may calculate at least one virtual plane as an index of the swing. For example, at least one virtual plane includes a shaft plane SP (an example of a first virtual plane) which will be described later, and a Hogan plane HP (an example of a second virtual plane) which will be described later forming a first angle with the shaft plane SP, and the swing analysis portion 211 may calculate the "shaft plane SP" and the "Hogan plane HP" as the indexes.

The swing analysis portion 211 may calculate a position of the head of the golf club 3 at a first timing during the backswing as an index of the swing. For example, the first timing is the time of halfway back at which the longitudinal direction of the golf club 3 becomes a direction along the horizontal direction during the backswing, and the swing analysis portion 211 may calculate a "position of the head at halfway back" which will be described later as the index.

The swing analysis portion 211 may calculate a position of the head of the golf club 3 at a second timing during the downswing as an index of the swing. For example, the second timing is the time of halfway down at which the longitudinal direction of the golf club 3 becomes a direction along the horizontal direction during the downswing, and the swing analysis portion 211 may calculate a "position of the head at halfway down" which will be described later as the index.

The swing analysis portion 211 may calculate an index based on an incidence angle of the head of the golf club 3 at impact (at ball hitting), as an index of the swing. For example, the swing analysis portion 211 may calculate a "club path (incidence angle) $\psi$" and an "attack angle" which will be described later as the index.

The swing analysis portion 211 may calculate an index based on an inclination of the head of the golf club 3 at impact (at ball hitting) as an index of the swing. For example, the swing analysis portion 211 may calculate a "(absolute) face angle $\phi$" or a "relative face angle $\eta$" which will be described later as the index.

The swing analysis portion 211 may calculate an index based on a speed of the head of the golf club 3 at impact (at ball hitting) as an index of the swing. For example, the swing analysis portion 211 may calculate a "head speed" which will be described later as the index.

The swing analysis portion 211 may calculate, as an index of the swing, an index based on a rotation angle about a rotation axis (hereinafter, referred to as about the long axis) of the shaft of the golf club 3 at a predetermined timing between the time of starting a backswing and the time of impact (at ball hitting) with the longitudinal direction of the shaft as the rotation axis. The rotation angle about the long axis of the golf club 3 may be an angle by which the golf club 3 is rotated about the long axis from a reference timing to a predetermined timing. The reference timing may be the time of starting a backswing, and may be the time of address. The predetermined timing may be the time (the time of a top) at which a backswing transitions to a downswing. For example, the swing analysis portion 211 may calculate a "shaft axis rotation angle $\theta_{top}$ at top" which will be described later as the index.

The swing analysis portion 211 may calculate an index based on a deceleration amount of the grip of the golf club 3 during the downswing as an index of the swing. For example, the swing analysis portion 211 may calculate a "grip deceleration ratio $R_V$" which will be described later as the index.

The swing analysis portion 211 may calculate an index based on a deceleration period of the grip of the golf club 3 during the downswing as an index of the swing. For example, the swing analysis portion 211 may calculate a "grip deceleration time ratio $R_T$" which will be described later as the index.

However, the swing analysis portion 211 may not calculate values of some of the indexes, and may calculate values of other indexes, as appropriate.

The image data generation portion 212 performs a process of generating image data corresponding to an image displayed on the display section 25. For example, the image data generation portion 212 generates image data corresponding to the selection screen illustrated in FIG. 7, and the display screen illustrated in FIG. 8, on the basis of various pieces of information received by the data acquisition portion 210.

The display processing portion 214 performs a process of displaying various images (including text, symbols, and the like in addition to an image corresponding to the image data generated by the image data generation portion 212) on the display section 25. For example, the display processing portion 214 displays the selection screen illustrated in FIG. 7, the input data editing screen illustrated in FIG. 8, and the like, on the display section 25, on the basis of the image data generated by the image data generation portion 212. For example, the image data generation portion 212 may display an image, text, or the like for notifying the user 2 of permission of swing starting on the display section 25 in step S5 in FIG. 4. For example, the display processing portion 214 may display text information such as text or symbols indicating an analysis result in the swing analysis portion 211 on the display section 25 automatically or in response to an input operation performed by the user 2 after a swing action of the user 2 is completed. Alternatively, a display section may be provided in the sensor unit 10, and the display processing portion 214 may transmit image data to the sensor unit 10 via the communication section 22, and various images, text, or the like may be displayed on the display section of the sensor unit 10.

The sound output processing portion 215 performs a process of outputting various sounds (including voices, buzzer sounds, and the like) from the sound output section 26. For example, the sound output processing portion 215 may output a sound for notifying the user 2 of permission of swing starting from the sound output section 26 in step S5 in FIG. 4. For example, the sound output processing portion 215 may output a sound or a voice indicating an analysis result in the swing analysis portion 211 from the sound output section 26 automatically or in response to an input operation performed by the user 2 after a swing action of the user 2 is completed. Alternatively, a sound output section may be provided in the sensor unit 10, and the sound output processing portion 215 may transmit various items of sound data or voice data to the sensor unit 10 via the communication section 22, and may output various sounds or voices from the sound output section of the sensor unit 10.

A vibration mechanism may be provided in the swing analysis apparatus 20 or the sensor unit 10, and various pieces of information may be converted into vibration pieces of information by the vibration mechanism so as to be presented to the user 2.

1-3. Swing Analysis Process

In the present embodiment, when a position of the head of the golf club 3 at address (during standing still) is set to the origin, an XYZ coordinate system (global coordinate system) is defined which has a target line indicating a target hit ball direction as an X axis, an axis on a horizontal plane which is perpendicular to the X axis as a Y axis, and a vertically upward direction (a direction opposite to the gravitational direction) as a Z axis. In order to calculate each index value, the swing analysis portion 211 calculates a position and an attitude of the sensor unit 10 in a time series from the time of the address in the XYZ coordinate system (global coordinate system) by using measured data (acceleration data and angular velocity data) in the sensor unit 10. The swing analysis portion 211 detects respective timings of the swing starting, the top, and the impact illustrated in FIG. 6, by using the measured data (acceleration data or angular velocity data) in the sensor unit 10. The swing analysis portion 211 calculates values of the respective indexes (for example, a shaft plane, a Hogan plane, a head position at halfway back, a head position at halfway down, a face angle, a club path (incidence angle), a shaft axis rotation angle at top, a head speed, a grip deceleration ratio, and a grip deceleration time ratio) of the swing by using the time series data of the position and the attitude of the sensor unit 10, and the timings of the swing starting, the top, and the impact, so as to generate the swing analysis data 248.

Calculation of Position and Attitude of Sensor Unit 10

If the user 2 performs the action in step S4 in FIG. 4, first, the swing analysis portion 211 determines that the user 2 stands still at an address attitude in a case where an amount of changes in acceleration data measured by the acceleration sensor 12 does not continuously exceed a threshold value for a predetermined period of time. Next, the swing analysis portion 211 computes an offset amount included in the measured data by using the measured data (acceleration data and angular velocity data) for the predetermined period of time. Next, the swing analysis portion 211 subtracts the offset amount from the measured data so as to perform bias correction, and computes a position and an attitude of the sensor unit 10 during a swing action of the user 2 (during the action in step S6 in FIG. 4) by using the bias-corrected measured data.

Specifically, first, the swing analysis portion 211 computes a position (initial position) of the sensor unit 10 during standing still (at address) of the user 2 in the XYZ coordinate system (global coordinate system) by using the acceleration data measured by the acceleration sensor 12, the golf club information 242, and the sensor attachment position information 246.

Figure 10:
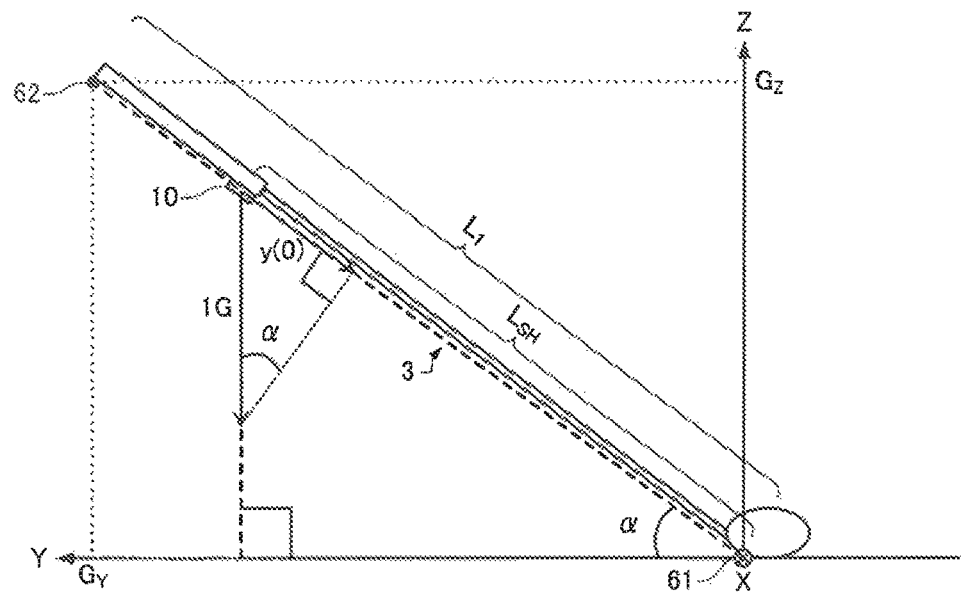
FIG. 10 is a plan view in which a golf club and the sensor unit are viewed from a negative side of an X axis during standing still of the user.

FIG. 10 is a plan view in which the golf club 3 and the sensor unit 10 during standing still (at address) of the user 2 are viewed from a negative side of the X axis. The origin O (0,0,0) is set at a position 61 of the head of the golf club 3, and coordinates of a position 62 of a grip end are (0, $G_Y, G_Z$). Since the user 2 performs the action in step S4 in FIG. 4, the position 62 of the grip end or the initial position of the sensor unit 10 has an X coordinate of 0, and is present on a YZ plane. As illustrated in FIG. 10, the gravitational acceleration of 1 G is applied to the sensor unit 10 during standing still of the user 2, and thus a relationship between a y axis acceleration y(0) measured by the sensor unit 10 and an inclined angle (an angle formed between the long axis of the shaft and the horizontal plane (XY plane)) α of the shaft of the golf club 3 is expressed by Equation (1).

$$y(0)=1 \ G \cdot \sin \alpha \tag{1}$$

Therefore, the swing analysis portion 211 can calculate the inclined angle α according to Equation (1) by using any acceleration data between any time points at address (during standing still).

Next, the swing analysis portion 211 subtracts a distance $L_{SG}$ between the sensor unit 10 and the grip end included in the sensor attachment position information 246 from a length $L_1$ of the shaft included in the golf club information 242, so as to obtain a distance $L_{SH}$ between the sensor unit 10 and the head. The swing analysis portion 211 sets, as the initial position of the sensor unit 10, a position separated by the distance $L_{SH}$ from the position 61 (origin O) of the head in a direction (a negative direction of the y axis of the sensor unit 10) specified by the inclined angle α of the shaft.

The swing analysis portion 211 integrates subsequent acceleration data so as to compute coordinates of a position from the initial position of the sensor unit 10 in a time series.

The swing analysis portion 211 computes an attitude (initial attitude) of the sensor unit 10 during standing still (at address) of the user 2 in the XYZ coordinate system (global coordinate system) by using acceleration data measured by the acceleration sensor 12. Since the user 2 performs the action in step S4 in FIG. 4, the x axis of the sensor unit 10 matches the X axis of the XYZ coordinate system in terms of direction at address (during standing still) of the user 2, and the y axis of the sensor unit 10 is present on the YZ plane. Therefore, the swing analysis portion 211 can specify the initial attitude of the sensor unit 10 on the basis of the inclined angle α of the shaft of the golf club 3.

The swing analysis portion 211 computes changes in attitudes from the initial attitude of the sensor unit 10 by performing rotation calculation using angular velocity data which is subsequently measured by the angular velocity sensor 14. An attitude of the sensor unit 10 may be expressed by, for example, rotation angles (a roll angle, a pitch angle, and a yaw angle) about the X axis, the Y axis, and the Z axis, or a quaternion.

The signal processing section 16 of the sensor unit 10 may compute an offset amount of measured data so as to perform bias correction on the measured data, and the acceleration sensor 12 and the angular velocity sensor 14 may have a bias correction function. In this case, it is not necessary for the swing analysis portion 211 to perform bias correction on the measured data.

Detection of Swing Starting, Top and Impact Timings

First, the swing analysis portion 211 detects a timing (impact timing) at which the user 2 hit a ball by using measured data. For example, the swing analysis portion 211 may compute a combined value of measured data (acceleration data or angular velocity data), and may detect an impact timing (time point) on the basis of the combined value.

Specifically, first, the swing analysis portion 211 computes a combined value $n_0(t)$ of angular velocities at each time point t by using the angular velocity data (bias-corrected angular velocity data for each time point t). For example, if the angular velocity data items at the time point t are respectively indicated by x(t), y(t), and z(t), the swing analysis portion 211 computes the combined value $n_0(t)$ of the angular velocities according to the following Equation (2).

$$n_0(t)=\sqrt{x(t)^2+y(t)^2+z(t)^2} \tag{2}$$

Next, the swing analysis portion 211 converts the combined value $n_0(t)$ of the angular velocities at each time point t into a combined value n(t) which is normalized (scale-conversion) within a predetermined range. For example, if the maximum value of the combined value of the angular velocities in an acquisition period of measured data is max($n_0$), the swing analysis portion 211 converts the combined value $n_0(t)$ of the angular velocities into the combined value n(t) which is normalized within a range of 0 to 100 according to the following Equation (3).

$$n(t) = \frac{100 \times n_0(t)}{\max(n_0)} \tag{3}$$

Next, the swing analysis portion 211 computes a derivative dn(t) of the normalized combined value n(t) at each time point t. For example, if a cycle for measuring three-axis angular velocity data items is indicated by Δt, the swing analysis portion 211 computes the derivative (difference) dn(t) of the combined value of the angular velocities at the time point t by using the following Equation (4).

$$dn(t)=n(t)-n(t-\Delta t) \tag{4}$$

Figure 11:
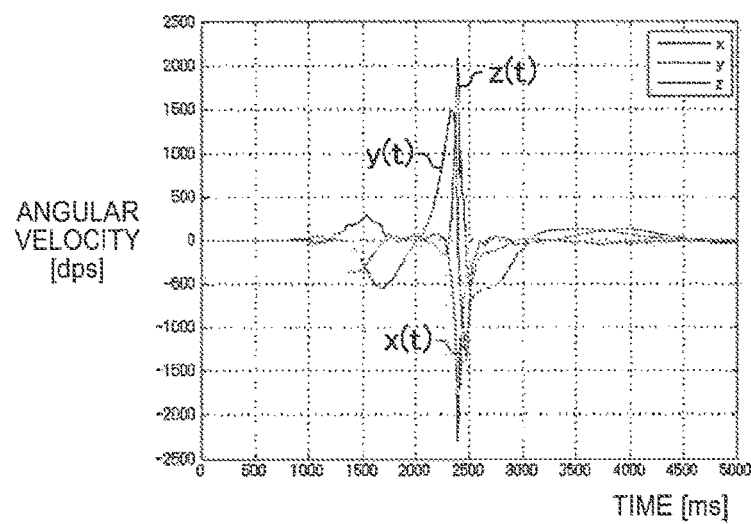
FIG. 11 is a graph illustrating examples of temporal changes of three-axis angular velocities.

FIG. 11 illustrates examples of three-axis angular velocity data items x(t), y(t) and z(t) obtained when the user 2 hits the golf ball 4 by performing a swing. In FIG. 11, a transverse axis expresses time (msec), and a longitudinal axis expresses angular velocity (dps).

Figure 12:
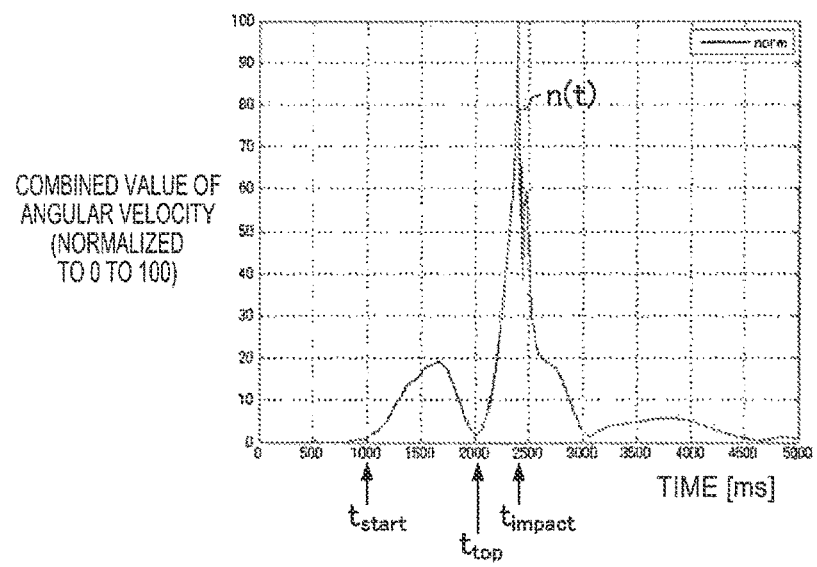
FIG. 12 is a graph illustrating a temporal change of a combined value of the three-axis angular velocities.

FIG. 12 is a diagram in which the combined value $n_0(t)$ of the three-axis angular velocities is computed according to Equation (2) by using the three-axis angular velocity data items x(t), y(t) and z(t) in FIG. 11, and then the combined value n(t) normalized to 0 to 100 according to Equation (3) is displayed in a graph. In FIG. 12, a transverse axis expresses time (msec), and a longitudinal axis expresses a norm of the angular velocity.

Figure 13:
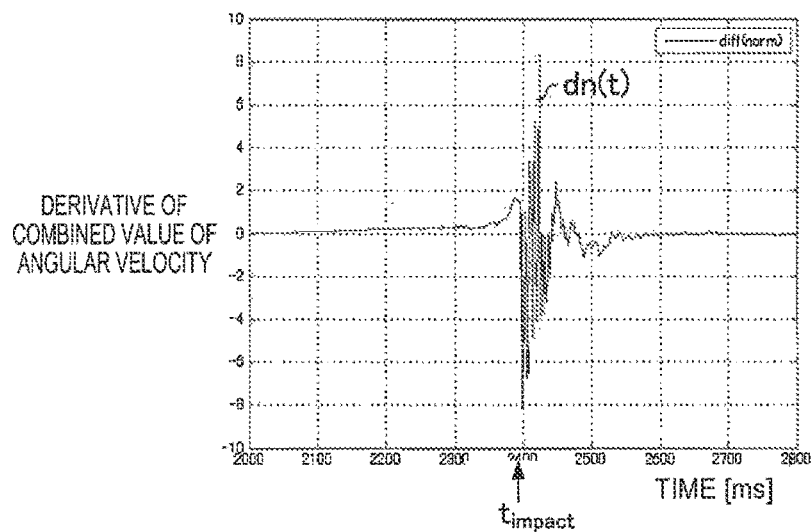
FIG. 13 is a graph illustrating a temporal change of a derivative of the combined value.

FIG. 13 is a diagram in which the derivative dn(t) is calculated according to Equation (4) on the basis of the combined value n(t) of the three-axis angular velocities in FIG. 12, and is displayed in a graph. In FIG. 13, a transverse axis expresses time (msec), and a longitudinal axis expresses a derivative value of the combined value of the three-axis angular velocities. In FIGS. 11 and 12, the transverse axis is displayed at 0 seconds to 5 seconds, but, in FIG. 13, the transverse axis is displayed at 2 seconds to 2.8 seconds so that changes in the derivative value before and after impact can be understood.

Next, of time points at which a value of the derivative dn(t) of the combined value becomes the maximum and the minimum, the swing analysis portion 211 specifies the earlier time point as an impact time point $t_{impact}$ (impact timing) (refer to FIG. 13). It is considered that swing speed is the maximum at the moment of impact in a typical golf swing. In addition, since it is considered that a value of the combined value of the angular velocities also changes according to a swing speed, the swing analysis portion 211 can capture a timing at which a derivative value of the combined value of the angular velocities is the maximum or the minimum (that is, a timing at which the derivative value of the combined value of the angular velocities is a positive maximum value or a negative minimum value) in a series of swing actions as the impact timing. Since the golf club 3 vibrates due to the impact, a timing at which a derivative value of the combined value of the angular velocities is the maximum and a timing at which a derivative value of the combined value of the angular velocities is the minimum may occur in pairs, and, of the two timings, the earlier timing may be the moment of the impact.

Next, the swing analysis portion 211 specifies a time point of a minimum point at which the combined value n(t) is close to 0 before the impact time point $t_{impact}$, as a top time point $t_{top}$ (top timing) (refer to FIG. 12). It is considered that, in a typical golf swing, an action temporarily stops at the top after starting the swing, then a swing speed increases, and finally impact occurs. Therefore, the swing analysis portion 211 can capture a timing at which the combined value of the angular velocities is close to 0 and becomes the minimum before the impact timing, as the top timing.

Next, the swing analysis portion 211 sets an interval in which the combined value n(t) is equal to or smaller than a predetermined threshold value before and after the top time point $t_{top}$, as a top interval, and detects a last time point at which the combined value n(t) is equal to or smaller than the predetermined threshold value before a starting time point of the top interval, as a swing starting (backswing starting) time point $t_{start}$ (refer to FIG. 12). It is hardly considered that, in a typical golf swing, a swing action is started from a standing still state, and the swing action is stopped till the top. Therefore, the swing analysis portion 211 can capture the last timing at which the combined value of the angular velocities is equal to or smaller than the predetermined threshold value before the top interval as a timing of starting the swing action. The swing analysis portion 211 may detect a time point of the minimum point at which the combined value n(t) is close to 0 before the top time point $t_{top}$ as the swing starting time point $t_{start}$.

The swing analysis portion 211 may also detect each of a swing starting timing, a top timing, and an impact timing by using three-axis acceleration data in the same manner.

Calculation of Shaft Plane and Hogan Plane

The shaft plane is a first virtual plane specified by a target line (target hit ball direction) and the longitudinal direction of the shaft of the golf club 3 at address (standing still state) of the user 2 before starting a swing. The Hogan plane is a second virtual plane specified by a virtual line connecting the vicinity of the shoulder (the shoulder or the base of the neck) of the user 2 to the head of the golf club (or the golf ball 4), and the target line (target hit ball direction), at address of the user 2.

Figure 14:
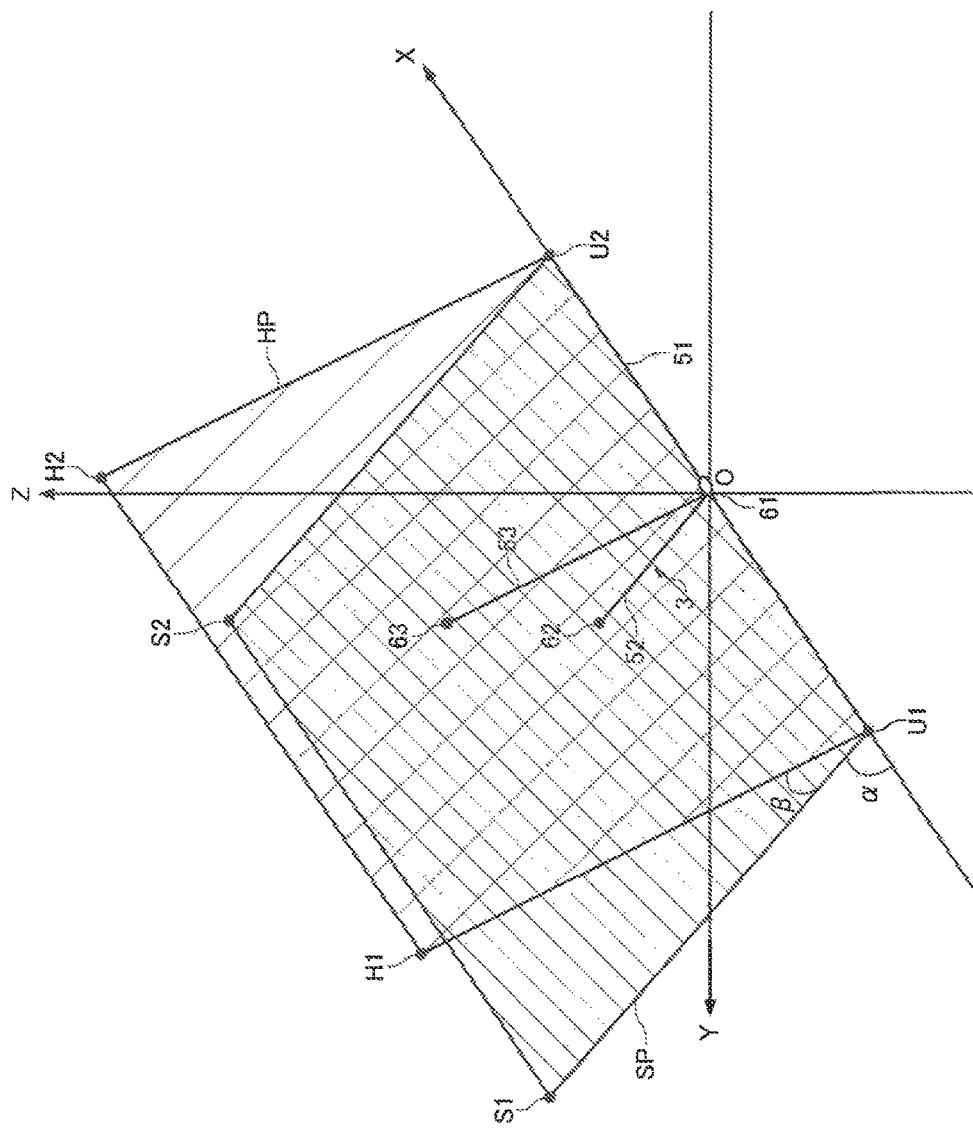
FIG. 14 is a diagram illustrating a shaft plane and a Hogan plane.

FIG. 14 is a diagram illustrating the shaft plane and the Hogan plane. FIG. 14 displays the X axis, the Y axis, and the Z axis of the XYZ coordinate system (global coordinate system).

As illustrated in FIG. 14, in the present embodiment, a virtual plane which includes a first line segment 51 as a first axis along a target hit ball direction and a second line segment 52 as a second axis along the longitudinal direction of the shaft of the golf club 3, and has four vertices such as U1, U2, S1, and S2, as the shaft plane SP (first virtual plane). In the present embodiment, the position 61 of the head of the golf club 3 at address is set as the origin O (0,0,0) of the XYZ coordinate system, and the second line segment 52 is a line segment connecting the position 61 (origin O) of the head of the golf club 3 to the position 62 of the grip end. The first line segment 51 is a line segment having a length UL in which U1 and U2 on the X axis are both ends, and the origin O is a midpoint. Since the user 2 performs the action in step S4 in FIG. 4 at address, and thus the shaft of the golf club 3 is perpendicular to the target line (X axis), the first line segment 51 is a line segment orthogonal to the longitudinal direction of the shaft of the golf club 3, that is, the second line segment 52. The swing analysis portion 211 calculates coordinates of the four vertices U1, U2, S1, and S2 of the shaft plane SP in the XYZ coordinate system.

Specifically, first, the swing analysis portion 211 computes coordinates $(0, G_Y, G_Z)$ of the position 62 of the grip end of the golf club 3 by using the inclined angle α and the length $L_1$ of the shaft included in the golf club information 242. As illustrated in FIG. 10, the swing analysis portion 211 may compute $G_Y$ and $G_Z$ by using the length $L_1$ of the shaft and the inclined angle α according to Equations (5) and (6).

$$G_Y = L_1 \cdot \cos \alpha \quad (5)$$

$$G_Z = L_1 \cdot \sin \alpha \quad (6)$$

Next, the swing analysis portion 211 multiplies the coordinates $(0, G_Y, G_Z)$ of the position 62 of the grip end of the golf club 3 by a scale factor S so as to compute coordinates $(0, S_Y, S_Z)$ of a midpoint S3 of the vertex S1 and the vertex S2 of the shaft plane SP. In other words, the swing analysis portion 211 computes $S_Y$ and $S_Z$ according to Equations (7) and (8), respectively.

$$S_Y = G_Y \cdot S \quad (7)$$

$$S_Z = G_Z \cdot S \quad (8)$$

Figure 15:
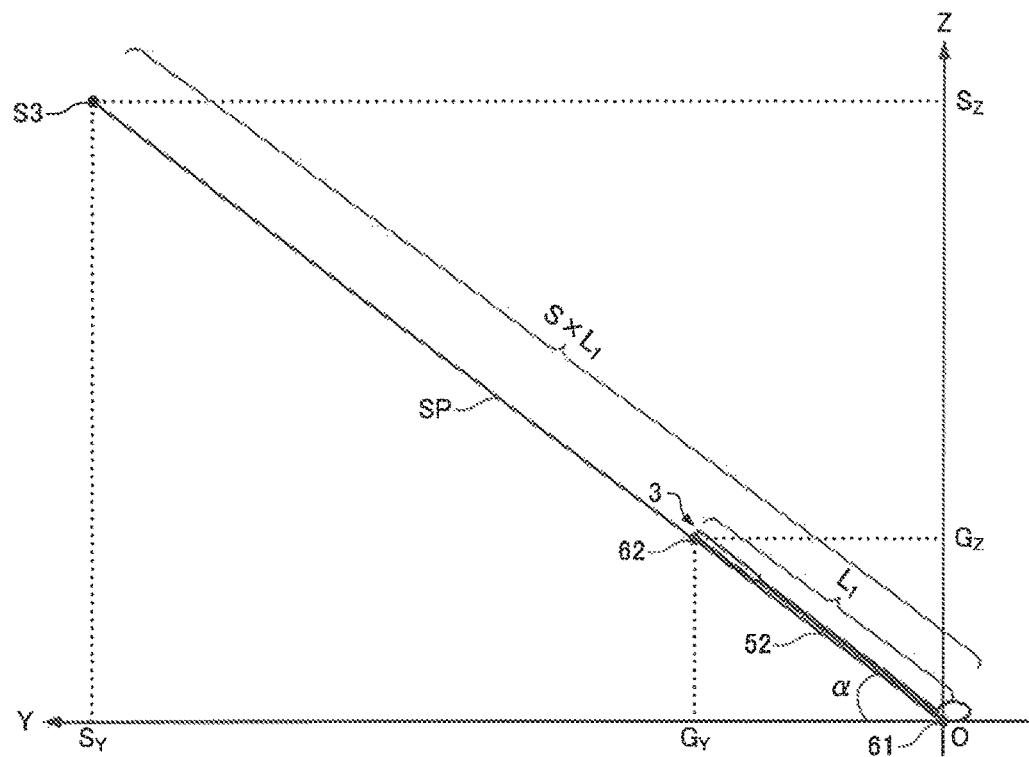
FIG. 15 is a view in which a sectional view of the shaft plane which is cut in a YZ plane is viewed from the negative side of the X axis.

FIG. 15 is a view in which a sectional view of the shaft plane SP in FIG. 14 which is cut in the YZ plane is viewed from the negative side of the X axis. As illustrated in FIG. 15, a length (a width of the shaft plane SP in a direction orthogonal to the X axis) of a line segment connecting the midpoint S3 of the vertex S1 and the vertex S2 to the origin O is S times the length $L_1$ of the second line segment 52. The scale factor S is set to a value at which a trajectory of the golf club 3 during a swing action of the user 2 enters the shaft plane SP. For example, if a length of the arms of the user 2 is indicated by $L_2$, the scale factor S may be set as in Equation (9) so that the width $S \times L_1$ of the shaft plane SP in the direction orthogonal to the X axis is twice the sum of the length $L_1$ of the shaft and the length $L_2$ of the arms.

$$S = \frac{2 \cdot (L_1 + L_2)}{L_1}. \quad (9)$$

The length $L_2$ of the arms of the user 2 is associated with a height $L_0$ of the user 2. The length $L_2$ of the arms is expressed by a correlation expression such as Equation (10) in a case where the user 2 is a male, and is expressed by a correlation expression such as Equation (11) in a case where the user 2 is a female, on the basis of statistical information.

$$L_2 = 0.41 \times L_0 - 45.5 \text{ [mm]} \quad (10)$$

$$L_2 = 0.46 \times L_0 - 126.9 \text{ [mm]} \quad (11)$$

Therefore, the swing analysis portion 211 may calculate the length $L_2$ of the arms of the user according to Equation (10) or Equation (11) by using the height $L_0$ and the sex of the user 2 included in the physical information 244.

Next, the swing analysis portion 211 computes coordinates $(-UL/2,0,0)$ of the vertex U1 of the shaft plane SP, coordinates $(UL/2,0,0)$ of a vertex U2, coordinates $(-UL/2, S_Y, S_Z)$ of the vertex S1, and coordinates $(UL/2, S_Y, S_Z)$ of the vertex S2 by using the coordinates $(0, S_Y, S_Z)$ of the midpoint S3 and a width (the length of the first line segment 51) UL of the shaft plane SP in the X axis direction. The width UL in the X axis direction is set to a value at which a trajectory of the golf club 3 during a swing action of the user 2 enters the shaft plane SP. For example, the width UL in the X axis direction may be set to be the same as the width $S \times L_1$ in the direction orthogonal to the X axis, that is, twice the sum of the length $L_1$ of the shaft and the length $L_2$ of the arms.

In the above-described manner, the swing analysis portion 211 can calculate the coordinates of the four vertices U1, U2, S1, and S2 of the shaft plane SP.

As illustrated in FIG. 14, in the present embodiment, a virtual plane which includes a first line segment 51 as a first axis and a third line segment 53 as a third axis, and has four vertices such as U1, U2, H1, and H2, is used as the Hogan plane HP (second virtual plane). The third line segment 53 is a line segment connecting a predetermined position 63 in the vicinity of a line segment connecting both of the shoulders of the user 2, to the position 61 of the head of the golf club 3. However, the third line segment 53 may be a line segment connecting the predetermined position 63 to a position of the golf ball 4. The swing analysis portion 211 calculates respective coordinates of the four vertices U1, U2, H1, and H2 of the Hogan plane HP in the XYZ coordinate system.

Specifically, first, the swing analysis portion 211 estimates the predetermined position 63 by using the coordinates $(0, G_Y, G_Z)$ of the position 62 of the grip end of the golf club 3 at address (during standing still), and the length $L_2$ of the arms of the user 2 based on the physical information 244, and computes coordinates $(A_X, A_Y, A_Z)$ thereof.

Figure 16:
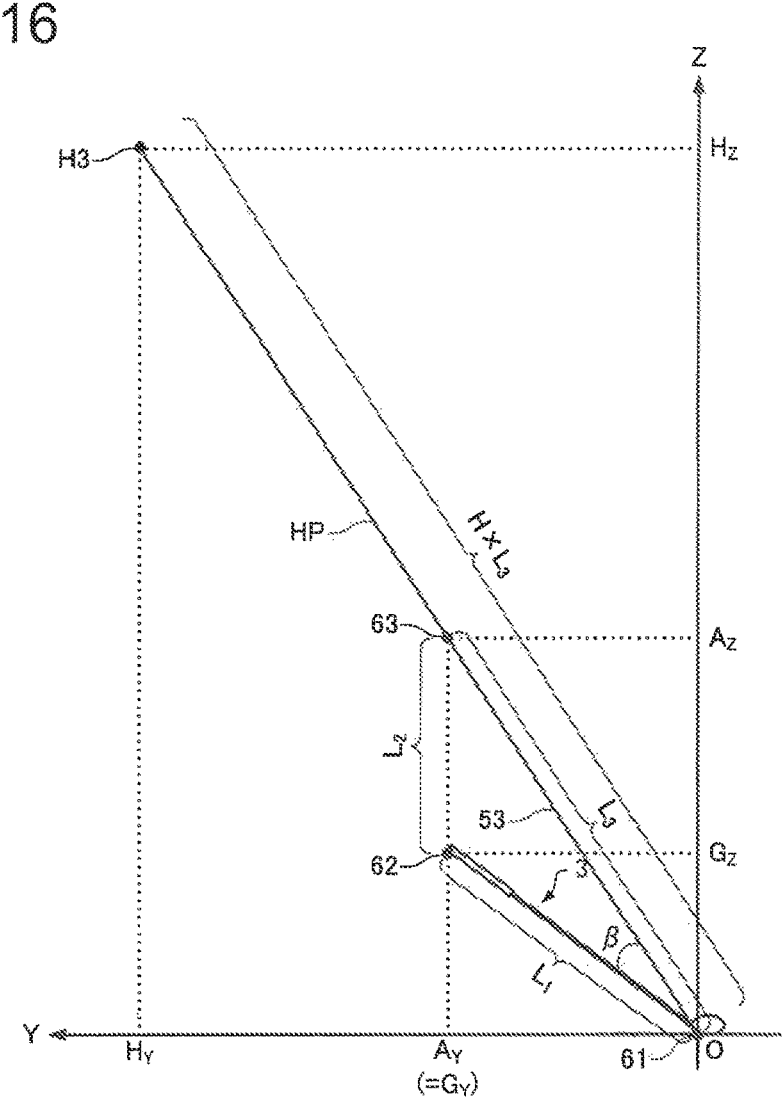
FIG. 16 is a view in which a sectional view of the Hogan plane which is cut in the YZ plane is viewed from the negative side of the X axis.

FIG. 16 is a view in which a sectional view of the Hogan plane HP illustrated in FIG. 14 which is cut in the YZ plane is viewed from the negative side of the X axis. In FIG. 16, a midpoint of the line segment connecting both of the shoulders of the user 2 is the predetermined position 63, and the predetermined position 63 is present on the YZ plane. Therefore, an X coordinate $A_X$ of the predetermined position 63 is 0. As illustrated in FIG. 16, the swing analysis portion 211 estimates, as the predetermined position 63, a position obtained by moving the position 62 of the grip end of the golf club 3 by the length $L_2$ of the arms of the user 2 in a positive direction along the Z axis. Therefore, the swing analysis portion 211 sets a Y coordinate $A_Y$ of the predetermined position 63 to be the same as the Y coordinate $G_Y$ of the position 62 of the grip end. The swing analysis portion 211 computes a Z coordinate $A_Z$ of the predetermined position 63 as a sum of the Z coordinate $G_Z$ of the position 62 of the grip end and the length $L_2$ of the arms of the user 2 as in Equation (12).

$$A_Z = G_Z + L_2 \quad (12)$$

Next, the swing analysis portion 211 multiplies the Y coordinate $A_Y$ and the Z coordinate $A_Z$ of the predetermined position 63 by a scale factor H, so as to compute coordinates $(0, H_Y, H_Z)$ of a midpoint H3 of the vertex H1 and the vertex H2 of the Hogan plane HP. In other words, the swing analysis portion 211 computes $H_Y$ and $H_Z$ according to Equation (13) and Equation (14), respectively.

$$H_Y = A_Y \cdot H \quad (13)$$

$$H_Z = A_Z \cdot H \quad (14)$$

As illustrated in FIG. 16, a length (a width of the Hogan plane HP in a direction orthogonal to the X axis) of a line segment connecting the midpoint H3 of the vertex H1 and the vertex H2 to the origin O is H times the length $L_3$ of the third line segment 53. The scale factor H is set to a value at which a trajectory of the golf club 3 during a swing action of the user 2 enters the Hogan plane HP. For example, the Hogan plane HP may have the same shape and the same size as the shape and the size of the shaft plane SP. In this case, the width $H \times L_3$ of the Hogan plane HP in the direction orthogonal to the X axis matches the width $S \times L_1$ of the shaft plane SP in the direction orthogonal to the X axis, and is twice the sum of the length $L_1$ of the shaft of the golf club 3 and the length $L_2$ of the arms of the user 2. Therefore, the swing analysis portion 211 may compute the scale factor H according to Equation (15).

$$H = \frac{2 \cdot (L_1 + L_2)}{L_3}. \quad (15)$$

The swing analysis portion 211 may compute the length $L_3$ of the third line segment 53 according to Equation (13) by using the Y coordinate $A_Y$ and the Z coordinate $A_Z$ of the predetermined position 63.

Next, the swing analysis portion 211 computes coordinates $(-UL/2, H_Y, H_Z)$ of the vertex H1 of the Hogan plane HP, and coordinates $(UL/2, H_Y, H_Z)$ of the vertex H2 by using the coordinates $(0, H_Y, H_Z)$ of the midpoint H3 and a width (the length of the first line segment 51) UL of the Hogan plane HP in the X axis direction. The two vertices U1 and U2 of the Hogan plane HP are the same as those of the shaft plane SP, and thus the swing analysis portion 211 does not need to compute coordinates of the vertices U1 and U2 of the Hogan plane HP again.

In the above-described manner, the swing analysis portion 211 can calculate the coordinates of the four vertices U1, U2, H1, and H2 of the Hogan plane HP.

A region interposed between the shaft plane SP (first virtual plane) and the Hogan plane HP (second virtual plane) is referred to as a "V zone", and a trajectory of a hit ball (a ball line) may be estimated to some extent on the basis of a relationship between a position of the head of the golf club 3 and the V zone during a backswing or a downswing. For example, in a case where the head of the golf club 3 is present in a space lower than the V zone at a predetermined timing during a backswing or a downswing, a hit ball is likely to fly in a hook direction. In a case where the head of the golf club 3 is present in a space higher than the V zone at a predetermined timing during a backswing or a downswing, a hit ball is likely to fly in a slice direction. In the present embodiment, as is clear from FIG. 16, a first angle β formed between the shaft plane SP and the Hogan plane HP is determined depending on the length $L_1$ of the shaft of the golf club 3 and the length $L_2$ of the arms of the user 2. In other words, since the first angle β is not a fixed value, and is determined depending on the type of golf club 3 or physical features of the user 2, the more appropriate shaft plane SP and Hogan plane HP (V zone) are calculated as an index for diagnosing a swing of the user 2.

Calculation of Head Positions at Halfway Back and Halfway Down

A head position at halfway back is a position of the head at the moment of the halfway back, right before the halfway back, or right after the halfway back, and a head position at halfway down is a position of the head at the moment of the halfway down, right before the halfway down, or right after the halfway down.

First, the swing analysis portion 211 computes a position of the head and a position of the grip end at each time point t by using the position and the attitude of the sensor unit 10 at each time point t from the swing start time point $t_{start}$ to the impact time point $t_{impact}$.

Specifically, the swing analysis portion 211 uses a position separated by the distance $L_{SH}$ in the positive direction of the y axis specified by the attitude of the sensor unit 10, from the position of the sensor unit 10 at each time point t, and computes coordinates of the position of the head. As described above, the distance $L_{SH}$ is a distance between the sensor unit 10 and the head. The swing analysis portion 211 uses a position separated by the distance $L_{SG}$ in the negative direction of the y axis specified by the attitude of the sensor unit 10, from the position of the sensor unit 10 at each time point t, and computes coordinates of the position of the grip end. As described above, the distance $L_{SG}$ is a distance between the sensor unit 10 and the grip end.

Next, the swing analysis portion 211 detects a halfway back timing and a halfway down timing by using the coordinates of the position of the head and the coordinates of the position of the grip end.

Specifically, the swing analysis portion 211 computes a difference ΔZ between a Z coordinate of the position of the head and a Z coordinate of the position of the grip end at each time point t from the swing start time point $t_{start}$ to the impact time point $t_{impact}$. The swing analysis portion 211 detects a time point $t_{HWB}$ at which a sign of ΔZ is inverted between the swing start time point $t_{start}$ and the top time point $t_{top}$, as the halfway back timing. The swing analysis portion 211 detects a time point $t_{HWD}$ at which a sign of ΔZ is inverted between the swing start time point $t_{top}$ and the top time point $t_{impact}$, as the halfway down timing.

The swing analysis portion 211 uses the position of the head at the time point $t_{HWB}$ as a position of the head at halfway back, and uses the position of the head at the time point $t_{HWD}$ as a position of the head at halfway down.

Calculation of Head Speed

A head speed is the magnitude of a speed of the head at impact (the moment of the impact, right before the impact, or right after the impact). For example, the swing analysis portion 211 computes a speed of the head at the impact time point $t_{impact}$ on the basis of differences between the coordinates of the position of the head at the impact time point $t_{impact}$ and coordinates of a position of the head at the previous time point. The swing analysis portion 211 computes the magnitude of the speed of the head as the head speed.

Calculation of Face Angle and Club Path (Incidence Angle)

The face angle is an index based on an inclination of the head of the golf club 3 at impact, and the club path (incidence angle) is an index based on a trajectory of the head of the golf club 3 at impact.

Figure 17:
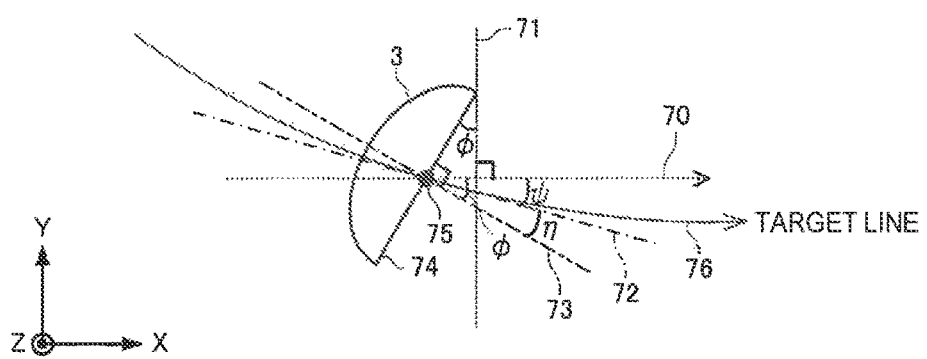
FIG. 17 is a diagram for explaining a face angle and a club path (incidence angle).

FIG. 17 is a diagram for explaining the face angle and the club path (incidence angle). FIG. 17 illustrates the golf club 3 (only the head is illustrated) on the XY plane viewed from a positive side of the Z axis in the XYZ coordinate system. In FIG. 17, the reference numeral 74 indicates a face surface (hitting surface) of the golf club 3, and the reference numeral 75 indicates a ball hitting point. The reference numeral 70 indicates a target line indicating a target hit ball direction, and the reference numeral 71 indicates a plane orthogonal to the target line 70. The reference numeral 76 indicates a curve indicating a trajectory of the head of the golf club 3, and the reference numeral 72 is a tangential line at the ball hitting point 75 for the curve 76. In this case, the face angle ϕ is an angle formed between the plane 71 and the face surface 74, that is, an angle formed between a straight line 73 orthogonal to the face surface 74, and the target line 70. The club path (incidence angle) ψ is an angle formed between the tangential line 72 (a direction in which the head in the XY plane passes through the ball hitting point 75) and the target line 70.

For example, assuming that an angle formed between the face surface of the head and the x axis direction is normally constant (for example, orthogonal), the swing analysis portion 211 computes a direction of a straight line orthogonal to the face surface on the basis of the attitude of the sensor unit 10 at the impact time point $t_{impact}$. The swing analysis portion 211 uses, a straight line obtained by setting a Z axis component of the direction of the straight line to 0, as a direction of the straight line 73, and computes an angle (face angle) ϕ formed between the straight line 73 and the target line 70.

For example, the swing analysis portion 211 uses a direction of a speed (that is, a speed of the head in the XY plane) obtained by setting a Z axis component of a speed of the head at the impact time point $t_{impact}$ to 0, as a direction of the tangential line 72, and computes an angle (club path (incidence angle)) ψ formed between the tangential line 72 and the target line 70.

The face angle ϕ indicates an inclination of the face surface 74 with the target line 70 whose direction is fixed regardless of an incidence direction of the head to the ball hitting point 75 as a reference, and is thus also referred to as an absolute face angle. In contrast, an angle η formed between the straight line 73 and the tangential line 72 indicates an inclination of the face surface 74 with an incidence direction of the head to the ball hitting point 75 as a reference, and is thus referred to as a relative face angle. The relative face angle η is an angle obtained by subtracting the club path (incidence angle) ψ from the (absolute) face angle ϕ.

Calculation of Attack Angle

An attack angle is an index based on a trajectory of the head of the golf club 3 at the impact time point $t_{impact}$ in the same manner as the club path (incidence angle). However, the attack angle is obtained as a result of an angle of a trajectory being computed in a plane which is different from the plane of the club path (incidence angle).

The swing analysis portion 211 computes an angle formed between a velocity vector of the head and the Z axis in the XZ plane at the impact time point $t_{impact}$, as the attack angle. For example, if a movement direction of the head at the impact time point $t_{impact}$ is a direction of a so-called upper blow, the attack angle is a positive value, the attack angle is a negative value in a direction of a so-called down blow, and the attack angle is zero in a direction of a level blow.

Calculation of Swing Rhythm

A swing rhythm is an index indicating a proportion of the time required in each section of a swing.

The swing analysis portion 211 partitions, for example, the entire swing period at the swing start time point $t_{start}$, the halfway back time point $t_{HWB}$, the top time point $t_{top}$, the halfway down time point $t_{HWD}$, the grip deceleration start time point $t_{vmax}$, and the impact time point $t_{impact}$, so as to divide the entire swing period into a plurality of sections, and computes the time required for each section.

The swing analysis portion 211 computes a ratio between the times required for two different sections, as a swing rhythm. Two different sections may be two sections not overlapping each other, and may be two sections one of which includes the other section. Two different sections may be two sections which are designated by the user 2 in advance.

For example, the swing analysis portion 211 computes a ratio obtained by dividing the time required for a backswing (the time required for the section from the swing start time point $t_{start}$ to the top time point $t_{top}$) by the time required for a downswing (the time required for the section from the top time point $t_{top}$ to the impact time point $t_{impact}$), as the swing rhythm.

Calculation of Hands-up Angle

A hands-up angle is one of indexes indicating an attitude deviation of the shaft between the swing start time point $t_{start}$ and the impact time point $t_{impact}$, and is an index indicating deviation between an inclined angle $\alpha$ ($t_{start}$) of the shaft in a lie angle direction at the swing start time point $t_{start}$ and an inclined angle $\alpha$ ($t_{impact}$) of the shaft in a lie angle direction at the impact time point $t_{impact}$. Instead of the inclined angle $\alpha$ ($t_{start}$) of the shaft in a lie angle direction at the swing start time point $t_{start}$, an inclined angle $\alpha$ ($t_{address}$) of the shaft in a lie angle direction at the address time point $t_{address}$ may be used. The inclined angle $\alpha$ in a lie angle direction is an angle indicated by the reference sign $\alpha$ in FIG. 10, and is an angle formed between the y axis and the Y axis in the YZ plane.

The swing analysis portion 211 calculates an inclined angle $\alpha$ ($t_{start}$) at the time of swing starting, for example, on the basis of an attitude (an attitude expressed in the global coordinate system) of the golf club 3 at the swing start time point $t_{start}$.

The swing analysis portion 211 calculates an inclined angle $\alpha$ ($t_{impact}$) at the impact time point $t_{impact}$, for example, on the basis of an attitude (an attitude expressed in the global coordinate system) of the golf club 3 at the impact time point $t_{impact}$.

The swing analysis portion 211 calculates an inclined angle $\alpha$ ($t_{address}$) at the address time point $t_{address}$, for example, on the basis of a ratio ($a_y/a_z$) between a z-axis acceleration component $a_z$ and a y-axis acceleration component $a_y$ at the address time point $t_{address}$. The swing analysis portion 211 may apply a y-axis acceleration component $a_y$ to "y(0)" in Equation (1) so as to obtain an inclined angle $\alpha$ ($t_{address}$) at the address time point.

For example, the swing analysis portion 211 subtracts the inclined angle $\alpha$ ($t_{start}$) at the swing start time point $t_{start}$ from the inclined angle $\alpha$ ($t_{impact}$) at the impact time point $t_{impact}$, so as to calculate an hands-up angle $\Delta\alpha = \alpha(t_{impact}) - \alpha(t_{start})$.

For example, the swing analysis portion 211 may subtract the inclined angle $\alpha(t_{address})$ at the swing start time point $t_{address}$ from the inclined angle $\alpha$ ($t_{impact}$) at the impact time point $t_{impact}$, so as to calculate an hands-up angle $\Delta\alpha = \alpha(t_{impact}) - \alpha(t_{address})$.

Calculation of Shaft Axis Rotation Angle at Top

The shaft axis rotation angle $\theta_{top}$ at top is an angle (relative rotation angle) by which the golf club 3 is rotated about a shaft axis from a reference timing to a top timing. The reference timing is, for example, the time of starting a backswing, or the time of address. In the present embodiment, in a case where the user 2 is a right-handed golfer, a right-handed screw tightening direction toward the tip end on the head side of the golf club 3 (a clockwise direction when the head is viewed from the grip end side) is a positive direction of the shaft axis rotation angle $\theta_{top}$. Conversely, in a case where the user 2 is a left-handed golfer, a left-handed screw tightening direction toward the tip end on the head side of the golf club 3 (a counterclockwise direction when the head is viewed from the grip end side) is a positive direction of the shaft axis rotation angle $\theta_{top}$.

Figure 18:
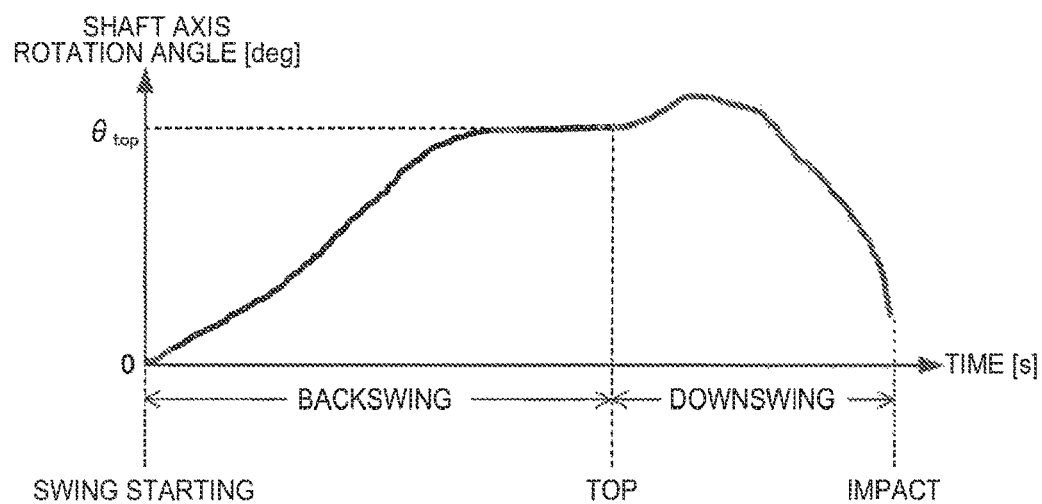
FIG. 18 is a diagram illustrating an example of a temporal change of a shaft axis rotation angle from swing starting (backswing starting) to impact.

FIG. 18 is a diagram illustrating an example of a temporal change of the shaft axis rotation angle from starting of a swing (starting of a backswing) to impact. In FIG. 18, a transverse axis expresses time (s), and a longitudinal axis expresses a shaft axis rotation angle (deg). FIG. 18 illustrates the shaft axis rotation angle $\theta_{top}$ at top with the time of starting a swing (the time of starting a backswing) as a reference timing (at which the shaft axis rotation angle is 0°).

In the present embodiment, as illustrated in FIG. 3, the y axis of the sensor unit 10 substantially matches the longitudinal direction of the shaft of the golf club 3 (the longitudinal direction of the golf club 3). Therefore, for example, the swing analysis portion 211 time-integrates a y axis angular velocity included in angular velocity data from the swing starting (backswing starting) time point $t_{start}$ or the time of address to the top time point $t_{top}$ (at top), so as to compute the shaft axis rotation angle $\theta_{top}$. Similarly, the swing analysis portion 211 time-integrates a y axis angular velocity included in angular velocity data from the swing starting (backswing starting) time point $t_{start}$ or the time of address to the halfway back time point $t_{HWB}$, so as to compute a shaft axis rotation angle $\theta_{HWB}$ at the halfway back time point $t_{HWB}$.

Calculation of Grip Deceleration Ratio and Grip Deceleration Time Ratio

The grip deceleration ratio is an index based on a grip deceleration amount, and is a ratio between a speed of the grip when the grip starts to be decelerated during the downswing, and a speed of the grip at impact. The grip deceleration time ratio is an index based on a grip deceleration period, and is a ratio between a period of time from the time at which the grip starts to be decelerated during the downswing to the time of impact, and a period of time of the downswing. A speed of the grip is preferably a speed of a portion held by the user 2, but may be a speed of any portion of the grip (for example, the grip end), and may be a speed of a peripheral portion of the grip.

Figure 19:
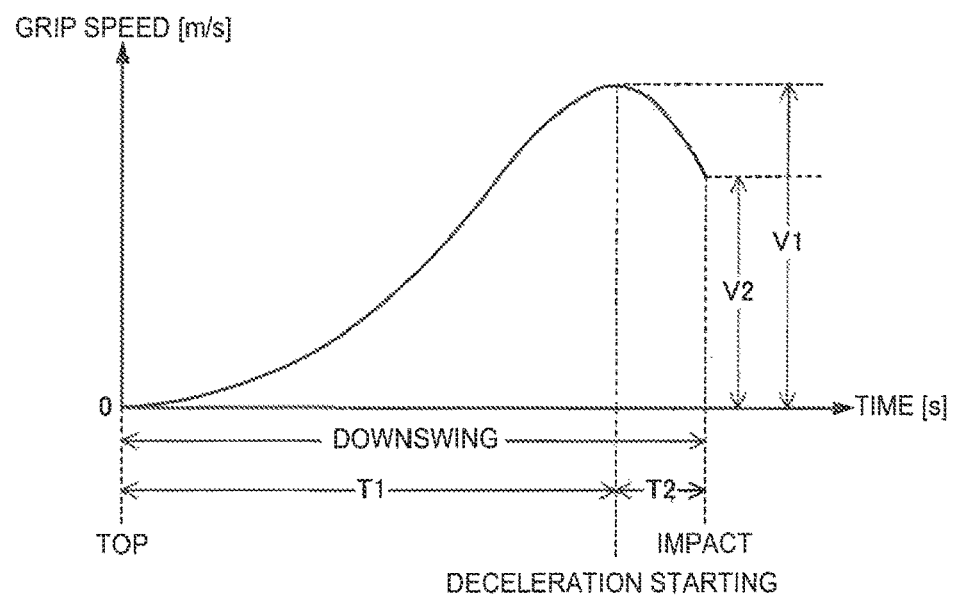
FIG. 19 is a diagram illustrating an example of a temporal change of a speed of a grip in a downswing.

FIG. 19 is a diagram illustrating an example of a temporal change of a speed of the grip during the downswing. In FIG. 19, a transverse axis expresses time (s), and a longitudinal axis expresses a speed (m/s) of the grip. In FIG. 19, if a speed (the maximum speed of the grip) when the grip starts to be decelerated is indicated by V1, and a speed of the grip at impact is indicated by V2, a grip deceleration ratio $R_V$ (unit: %) is expressed by the following Equation (16).

$$R_V = \frac{V1 - V2}{V1} \times 100\,(\%) \tag{16}$$

In FIG. 19, if a period of time from the time of top to the time at which the grip starts to be decelerated is indicated by T1, and a period of time from the time at which the grip starts to be decelerated during the downswing to the time of impact is indicated by T2, a grip deceleration time ratio $R_T$ (unit: %) is expressed by the following Equation (17).

$$R_T = \frac{T2}{T1 + T2} \times 100\,(\%) \tag{17}$$

For example, the sensor unit 10 may be attached to the vicinity of a portion of the golf club 3 held by the user 2, and a speed of the sensor unit 10 may be regarded as a speed of the grip. Therefore, first, the swing analysis portion 211 computes a speed of the sensor unit 10 at the time point t on the basis of differences between coordinates of a position of the sensor unit 10 at each time point t from the top time point $t_{top}$ to the impact time point $t_{impact}$ (during the downswing) and coordinates of a position of the sensor unit 10 at the previous time point.

Next, the swing analysis portion 211 computes the magnitude of the speed of the sensor unit 10 at each time point t, sets the maximum value thereof as V1, and sets the magnitude of the speed at the impact time point $t_{impact}$ as V2. The swing analysis portion 211 specifies a time point $t_{vmax}$ at which the magnitude of the speed of the sensor unit 10 becomes the maximum value V1. The swing analysis portion 211 computes T1=$t_{vmax}$-$t_{top}$, and T2=$t_{impact}$-$t_{vmax}$. The swing analysis portion 211 computes the grip deceleration ratio $R_V$ and the grip deceleration time ratio $R_T$ according to Equations (16) and (17), respectively.

The swing analysis portion 211 may regard a speed of the grip end as a speed of the grip, and may compute the speed of the grip end on the basis of coordinates of a position of the grip end at each time point t during the downswing, so as to obtain the grip deceleration ratio $R_V$ and the grip deceleration time ratio $R_T$ through the above-described computation.

Calculation of Indexes of "V Zone" Item

The swing analysis portion 211 calculates, as indexes, a region in which a head position is included at the halfway back time point $t_{HWB}$, a region in which a head position is included at the halfway down time point $t_{HWD}$, a region in which a head position is included at the grip deceleration start time point $t_{vmax}$, and a region in which a head position is included at the top time point $t_{top}$. Interfaces of a plurality of regions are determined on the basis of the shaft plane SP and the Hogan plane HP (V zone) which are virtual planes defined according to an address attitude of the user 2.

FIG. 20 is a diagram illustrating examples of relationships among the shaft plane SP and the Hogan plane HP (V zone), and a plurality of regions (a lower part in FIG. 20 schematically illustrates an example of the shaft plane SP, the Hogan plane HP, and an attitude of the user 2). FIG. 20 illustrates relationships among the shaft plane SP, the Hogan plane HP, and five regions A to E when viewed from a negative side of the X axis (when projected onto the YZ plane). The region B is a predetermined space including the Hogan plane HP, and the region D is a predetermined space including the shaft plane SP. The region C is a region interposed between the region B and the region D (a space between an interface $S_{BC}$ with region B and an interface $S_{CD}$ with the region D). The region A is a space in contact with the region B in an interface $S_{AB}$ on an opposite side to the region C. The region E is a space in contact with the region D in an interface $S_{DE}$ on an opposite side to the region C.

There may be various methods of setting the interface $S_{AB}$, the interface $S_{BC}$, the interface $S_{CD}$, and the interface $S_{DE}$. As an example, the interfaces may be set so that, on the YZ plane, the Hogan plane HP is located exactly at the center of the interface $S_{AB}$ and the interface $S_{BC}$, the shaft plane SP is located exactly at the center of the interface $S_{CD}$ and the interface $S_{DE}$, and angles of the region B, the region C, and the region D about the origin O (X axis) are the same as each other. In other words, with respect to the first angle β formed between the shaft plane SP and the Hogan plane HP, if each of angles formed between the Hogan plane HP, and the interface $S_{AB}$ and the interface $S_{BC}$ is set to β/4, and each of angles formed between the shaft plane SP, and the interface $S_{CD}$ and the interface $S_{DE}$ is set to β/4, angles of the region B, the region C, and the region D are all set to β/2.

Since a swing that causes a Y coordinate of a head position at halfway back or halfway down to be negative cannot be expected, an interface of the region A opposite to the interface $S_{AB}$ is set in the XZ plane in FIG. 20. Similarly, a swing that causes a Z coordinate of a head position at halfway back or halfway down to be negative cannot be expected, and an interface of the region E opposite to the interface $S_{DE}$ is set in the XY plane. Of course, an interface of the region A or the region E may be set so that an angle of the region A or the region E about the origin O (X axis) is the same as angles of the region B, the region C, and the region D.

Specifically, first, the swing analysis portion 211 sets the interface $S_{AB}$, the interface $S_{BC}$, the interface $S_{CD}$, and the interface $S_{DE}$ of the regions A to E on the basis of coordinates of each of the four vertices U1, U2, S1, and S2 of the shaft plane SP and coordinates of each of the four vertices U1, U2, H1, and H2 of the Hogan plane HP.

Next, the swing analysis portion 211 determines in which region of the regions A to E coordinates of a head position at the halfway back time point $t_{HWB}$, coordinates of a head position at the halfway down time point $t_{HWD}$, coordinates of a head position at the grip deceleration start time point $t_{vmax}$, and coordinates of a head position at the top time point $t_{top}$ are included.

Procedures of Swing Analysis Process

Figure 21:
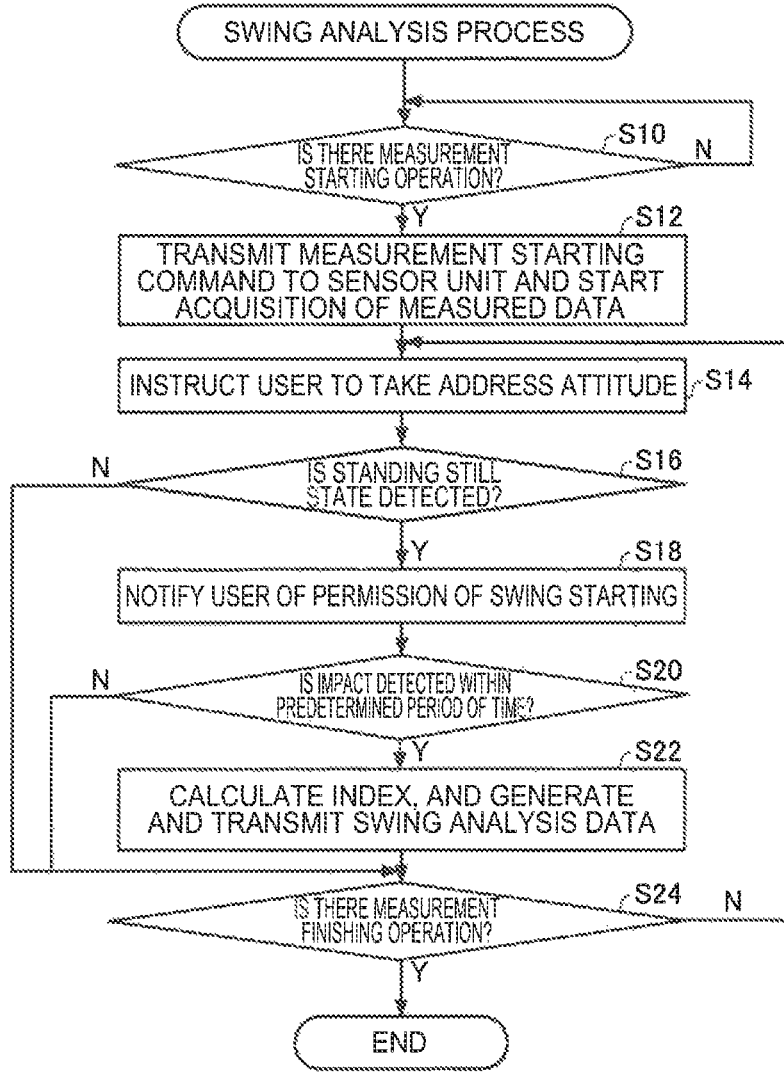
FIG. 21 is a flowchart illustrating examples of procedures of a swing analysis process (swing analysis method).

FIG. 21 is a flowchart illustrating examples of procedures of a swing analysis process performed by the processing section 21. The processing section 21 performs the swing analysis process, for example, according to the procedures shown in the flowchart of FIG. 21 by executing the swing analysis program 240 stored in the storage section 24. Hereinafter, the flowchart of FIG. 21 will be described.

First, the processing section 21 waits for the user 2 to perform a measurement starting operation (the operation in step S2 in FIG. 4) (N in step S10), transmits a measurement starting command to the sensor unit 10 if the measurement starting operation is performed (Y in step S10), and starts to acquire measured data from the sensor unit 10 (step S12).

Next, the processing section 21 instructs the user 2 to take an address attitude (step S14). The user 2 takes the address attitude in response to the instruction, and stands still (step S4 in FIG. 4).

Next, the processing section 21 determines whether or not the golf club 3 stands still at an accurate attitude for a predetermined period of time by using the measured data acquired from the sensor unit 10 (step S16), and notifies the user 2 of permission of swing starting (step S18) if the golf club stands still (Yin step S16), and proceeds to a finish determination process (step S24) if the golf club does not stand still. The processing section 21 outputs, for example, a predetermined sound, or an LED is provided in the sensor unit 10, and the LED is lighted, so that the user 2 is notified of permission of swing starting. The user 2 confirms the notification and then starts a swing action (the action in step S6 in FIG. 4).

Next, the processing section 21 determines whether or not impact is detected within a predetermined period from the permission of the swing (step S18) on the basis of the measured data acquired from the sensor unit 10 (step S20), proceeds to a swing analysis data generation process (step S22) if the impact is detected (Y in step S20), and proceeds to the finish determination process (step S24) if the impact is not detected (N in step S20).

Next, the processing section 21 extracts measured data during the swing before and after the impact, from the measured data acquired from the sensor unit 10, calculates various indexes and trajectories on the basis of the measured data during the swing, generates swing analysis data including the indexes and the trajectories, and transmits the swing analysis data to the server apparatus 30 (step S22). The processing section 21 uses the measured data in the period in which the golf club 3 stands still at an accurate attitude, for performing bias correction on the measured data during the swing and setting global coordinates. The processing section 21 may cause the measured data itself (so-called raw data) during the swing to be included in the swing analysis data which is transmitted to the server apparatus 30.

Next, the processing section 21 determines whether or not a measurement finishing operation has been performed by the user 2 (step S24), finishes the flow if the operation has been performed (Y in step S24), and proceeds to the address instruction process (step S14) if the operation has not been performed (N in step S24).

In the flowchart of FIG. 21, order of the respective steps may be changed as appropriate within an allowable range, some of the steps may be omitted or changed, and other steps may be added thereto.

1-4. Configuration of Swing Diagnosis Apparatus

Figure 22:
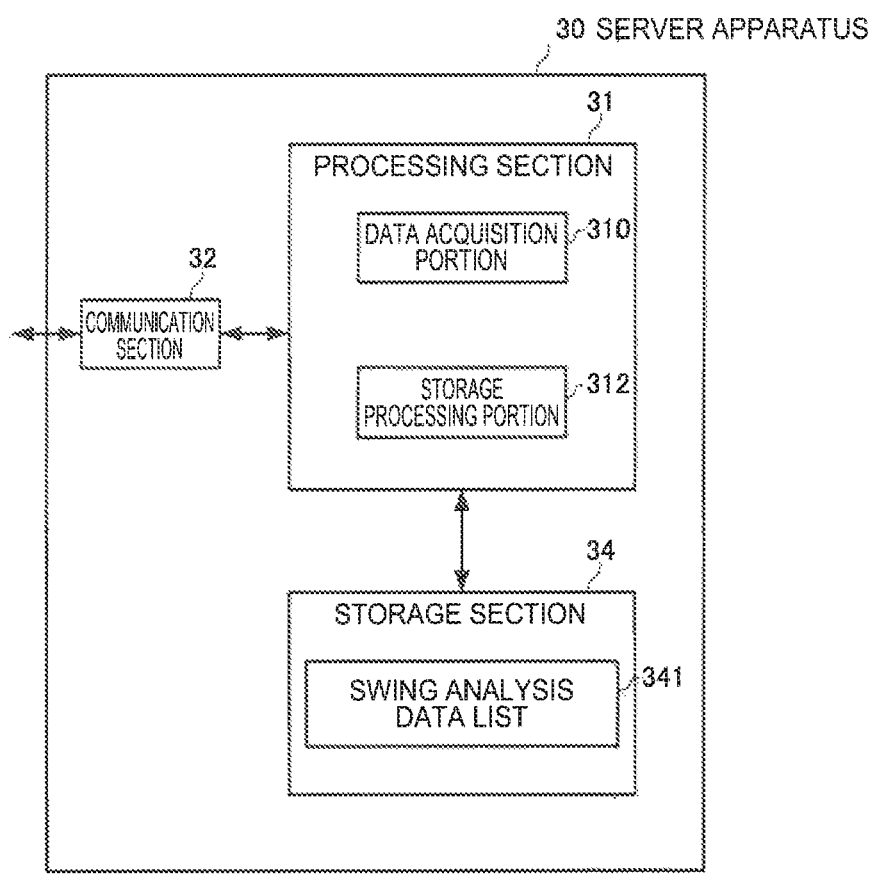
FIG. 22 is a diagram illustrating a configuration example of a server apparatus.

FIG. 22 is a diagram illustrating a configuration example of the server apparatus 30. As illustrated in FIG. 22, in the present embodiment, the server apparatus 30 is configured to include a processing section 31, a communication section 32, and a storage section 34. However, the server apparatus 30 may have a configuration in which some of the constituent elements are deleted or changed as appropriate, or may have a configuration in which other constituent elements are added thereto. The processing section 31 is constituted of a processing device such as a CPU or other processor.

The storage section 34 is constituted of, for example, various IC memories such as a ROM, a flash ROM, and a RAM, or a recording medium such as a hard disk or a memory card. The storage section 34 stores a program for the processing section 31 performing various calculation processes or a control process, or various programs or data for realizing application functions.

In the present embodiment, the storage section 34 stores (preserves) a swing analysis data list 341 including a plurality of items of swing analysis data 248 generated by the swing analysis apparatus 20. In other words, the swing analysis data 248 generated whenever the processing section 21 of the swing analysis apparatus 20 analyzes a swing action of the user 2 is sequentially added to the swing analysis data list 341.

The storage section 34 is used as a work area of the processing section 31, and temporarily stores results of calculation executed by the processing section 31 according to various programs, and the like. The storage section 34 may store data which is required to be preserved for a long period of time among data items generated through processing of the processing section 31.

The communication section 32 performs data communication with the communication section 27 (refer to FIG. 9) of the swing analysis apparatus 20 via the network 40. For example, the communication section 32 performs a process of receiving the swing analysis data 248 from the communication section 27 of the swing analysis apparatus 20, and transmitting the swing analysis data 248 to the processing section 31. For example, the communication section 32 performs a process of transmitting information required to display the selection screen illustrated in FIG. 7 to the communication section 27 of the swing analysis apparatus 20, or a process of receiving selected information on the selection screen illustrated in FIG. 7 from the communication section 27 of the swing analysis apparatus 20 and transmitting the selected information to the processing section 31. For example, the communication section 32 performs a process of receiving information required to display the display screen illustrated in FIG. 8 from the processing section 31, and transmitting the information to the communication section 27 of the swing analysis apparatus 20.

The processing section 31 performs a process of receiving the swing analysis data 248 from the swing analysis apparatus 20 via the communication section 32 and storing the swing analysis data 248 in the storage section 34 (adding the swing analysis data to the swing analysis data list 341), according to various programs. The processing section 31 performs a process of receiving various pieces of information from the swing analysis apparatus 20 via the communication section 32, and transmitting information required to display various screens (the respective screens illustrated in FIGS. 7 and 8) to the swing analysis apparatus 20, according to various programs. The processing section 31 performs other various control processes.

Particularly, in the present embodiment, the processing section 31 functions as a data acquisition portion 310 and a storage processing portion 312 by executing a predetermined program.

The data acquisition portion 310 performs a process of receiving the swing analysis data 248 received from the swing analysis apparatus 20 by the communication section 32 and transmitting the swing analysis data 248 to the storage processing portion 312.

The storage processing portion 312 performs read/write processes of various programs or various data for the storage section 34. For example, the storage processing portion 312 performs a process of receiving the swing analysis data 248 from the data acquisition portion 310 and storing the swing analysis data 248 in the storage section 34 (adding the swing analysis data to the swing analysis data list 341), a process of reading the swing analysis data 248 from the swing analysis data list 341 stored in the storage section 34, or the like.

1-5. Process in Server Apparatus

The processing section 31 of the server apparatus 30 transmits and receives data to and from the swing analysis apparatus 20, and thus manages user swing analysis data for each user.

Procedures of Process in Server Apparatus

Figure 23:
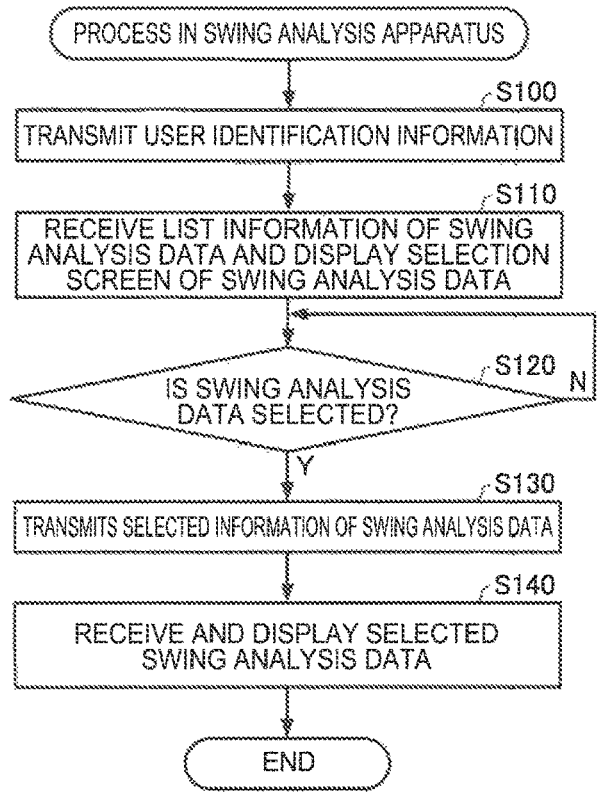
FIG. 23 is a flowchart illustrating examples of procedures of a process performed by a swing analysis apparatus in relation to the server apparatus.
Figure 24:
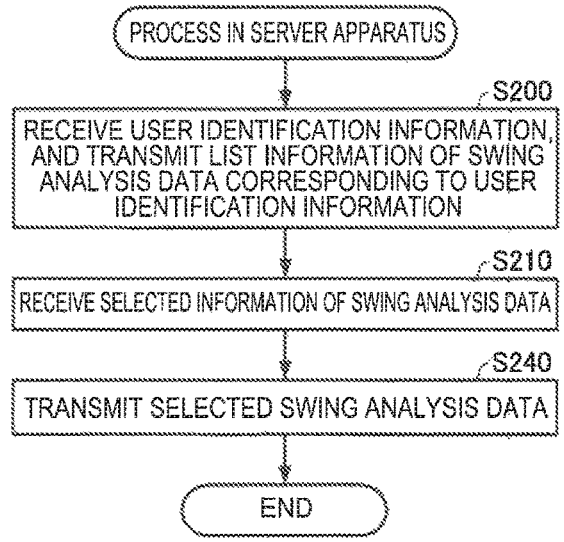
FIG. 24 is a flowchart illustrating examples of procedures of a process performed by the server apparatus.

FIG. 23 is a flowchart illustrating examples of procedures of a process performed by the processing section 21 of the swing analysis apparatus 20 in relation to a process in the server apparatus. FIG. 24 is a flowchart illustrating examples of procedures of a process in the server apparatus. The processing section 31 (an example of a computer) of the server apparatus 30 performs a process, for example, according to the procedures of the flowchart of FIG. 24 by executing the program stored in the storage section 34. Hereinafter, the flowcharts of FIGS. 23 and 24 will be described.

First, the processing section 21 of the swing analysis apparatus 20 transmits user identification information allocated to the user 2, to the server apparatus 30 (step S100 in FIG. 23).

Next, the processing section 31 of the server apparatus 30 receives the user identification information, and transmits list information of the swing analysis data 248 corresponding to the user identification information (step S200 in FIG. 24).

Next, the processing section 21 of the swing analysis apparatus 20 receives the list information of the swing analysis data 248, and displays a selection screen (FIG. 7) of the swing analysis data on the display section 25 (step S110 in FIG. 23).

The processing section 21 of the swing analysis apparatus 20 waits for the swing analysis data 248 to be selected on the selection screen of the swing analysis data (N in step S120 in FIG. 23), and transmits selected information of the swing analysis data to the server apparatus 30 (step S130 in FIG. 23) if the information is selected (Y in step S120 in FIG. 23).

Next, the processing section 31 of the server apparatus 30 receives the selected information of the swing analysis data (step S210 in FIG. 24).

Next, the processing section 31 of the server apparatus 30 transmits the selected swing analysis data (step S240 in FIG. 24).

Next, the processing section 21 of the swing analysis apparatus 20 receives the selected swing analysis data, displays images (images indicating various indexes, an image indicating a swing trajectory, and the like) based on the swing analysis data on the display section 25 (step S140 in FIG. 23), and finishes the process.

In the flowchart of FIG. 23, order of the respective steps may be changed as appropriate within an allowable range, some of the steps may be omitted or changed, and other steps may be added thereto. Similarly, in the flowchart of FIG. 24, order of the respective steps may be changed as appropriate within an allowable range, some of the steps may be omitted or changed, and other steps may be added thereto.

1-6. V Zone Item 1-6-1. Score and Diagnosis Information of V Zone Item

The swing analysis apparatus 20 of the present embodiment calculates indexes (four indexes) of the above-described V zone item as swing analysis data, and acquires a score of the V zone item and diagnosis information of the V zone item on the basis of the four indexes. The four indexes of the V zone item will be described again as in the following (1) to (4).

(1) Of the regions A to E, a region in which a head process is included at the halfway back time point $t_{HWB}$ (the time point $t_{HWB}$ is an example of a timing at which the longitudinal direction of an exercise appliance during a backswing is along the horizontal plane)

(2) Of the regions A to E, a region in which a head process is included at the top time point $t_{top}$ (the time point $t_{top}$ is an example of a timing of a top)

(3) Of the regions A to E, a region in which a head process is included at the grip deceleration start time point $t_{vmax}$ (natural uncock point) (the time point $t_{vmax}$ is an example of a timing which a holding portion of an exercise appliance starts to decelerate during a downswing)

(4) Of the regions A to E, a region in which a head process is included at the halfway down time point $t_{HWD}$ (the time point $t_{HWD}$ is an example of a timing at which the longitudinal direction of an exercise appliance during a downswing is along the horizontal plane)

The storage section 24 of the swing analysis apparatus 20 stores a V zone correspondence table as illustrated in FIG. 25 in advance.

As illustrated in FIG. 25, in the V zone correspondence table, a score and diagnosis information are allocated to each arrangement pattern (hereinafter, referred to as a "region arrangement pattern") in which the four indexes of the V zone item are arranged in a time series.

For example, in the V zone correspondence table illustrated in FIG. 25, a score allocated to a region arrangement pattern "A-A-A-A" is PV1, and diagnosis information allocated to the region arrangement pattern "A-A-A-A" is LV1.

Here, in the V zone correspondence table illustrated in FIG. 25, a score (level) and diagnosis information for each region arrangement pattern are set in advance on the basis of relationships among region arrangement patterns for various swings and tendencies of hit ball trajectories for various swings.

For example, a relatively low score is allocated to a region arrangement pattern for a swing in which a trajectory is likely to be deviated relative to a target line, and a relatively high score is allocated to a region arrangement pattern for a swing in which a trajectory is unlikely to be deviated relative to a target line. For example, the highest score (5 points) is allocated to a region arrangement pattern (for example, "C-C-C-C") for a swing in which a trajectory is most unlikely to be deviated relative to a target line, and the lowest score (1 point) is allocated to a region arrangement pattern for a swing in which a trajectory is most likely to be deviated relative to a target line.

For example, diagnosis information indicating that a swing type is a hook type is allocated to a region arrangement pattern for a swing in which a trajectory is likely to be hooked, and diagnosis information indicating that a swing type is a slice type is allocated to a region arrangement pattern for a swing in which a trajectory is likely to be sliced.

Meanwhile, an ideal swing or a standard swing causes an arrangement pattern (hereinafter, referred to as a "timing arrangement pattern") in which the above-described four time points $t_{HWB}$, $t_{top}$, $t_{vmax}$, and $t_{HWD}$ are arranged in a time series (order of arriving timings), such as "$t_{HWB}$-$t_{top}$-$t_{vmax}$-$t_{HWD}$" as illustrated in FIG. 25. However, a swing which is not ideal may cause a timing arrangement pattern such as "$t_{HWB}$-$t_{top}$-$t_{HWD}$-$t_{vmax}$".

Thus, a lower score is preferably allocated to a case where a timing arrangement pattern is "$t_{HWB}$-$t_{top}$-$t_{HWD}$-$t_{vmax}$" than a case where a timing arrangement pattern is "$t_{HWB}$-$t_{top}$-$t_{vmax}$-$t_{HWD}$". In addition, diagnosis information indicating that a deceleration start timing of the wrist is later than an ideal timing is preferably allocated to a case where a timing arrangement pattern is "$t_{HWB}$-$t_{top}$-$t_{HWD}$-$t_{vmax}$".

In order to perform the allocation, for example, the storage section 24 stores, as the V zone correspondence table, two correspondence tables such as a correspondence table (hereinafter, referred to as a "first V zone correspondence table") which is applied in a case where a timing arrangement pattern is "$t_{HWB}$-$t_{top}$-$t_{vmax}$-$t_{HWD}$" and a correspondence table (hereinafter, referred to as a "second V zone correspondence table") which is applied in a case where a timing arrangement pattern is "$t_{HWB}$-$t_{top}$-$t_{HWD}$-$t_{vmax}$". The second V zone correspondence table is not illustrated.

1-6-2. Process of Acquiring Score and Diagnosis Information

The swing analysis portion 211 of the swing analysis apparatus 20 acquires a score and diagnosis information of the V zone item in the above step S22 (FIG. 21) according to, for example, the following procedures (1) to (4).

(1) The swing analysis portion 211 determines whether a timing arrangement pattern is "$t_{HWB}$-$t_{top}$-$t_{vmax}$-$t_{HWD}$" or "$t_{HWB}$-$t_{top}$-$t_{HWD}$-$t_{vmax}$" on the basis of the four time points of the V zone item.

(2) The swing analysis portion 211 recognizes a region arrangement pattern on the basis of a determination result of the procedure (1) and the four indexes of the V zone item.

(3) In a case where a timing arrangement pattern is "$t_{HWB}$-$t_{top}$-$t_{vmax}$-$t_{HWD}$", the swing analysis portion 211 acquires a score and diagnosis information of the V zone item by referring to the first V zone correspondence table according to the region arrangement pattern.

(4) In a case where a timing arrangement pattern is "$t_{HWB}$-$t_{top}$-$t_{HWD}$-$t_{vmax}$", the swing analysis portion 211 acquires a score and diagnosis information of the V zone item by referring to the second V zone correspondence table according to the region arrangement pattern.

The score, the diagnosis, the region arrangement pattern, and the timing arrangement pattern acquired according to the above procedures (1) to (4) are included in swing analysis data along with various indexes.

In the above description, the swing analysis portion 211 uses a "score" as information indicating a level of the V zone item, but may use information other than a score, for example, "rank 1, rank 2, rank 3, . . . ", "A rank, B rank, C rank, . . . ", "◯, X, Δ, . . . ", "high level, middle level, low level, . . . " (however, hereinafter, a "score" is assumed to be used as a level of the V zone item).

1-6-3. Display Screen of V Zone Item

In the present embodiment, if the user 2 checks any one of the checkboxes so as to select swing analysis data regarding a single swing on the selection screen illustrated in FIG. 7, then presses the OK button (taps the button with the fingertip) located on the lower part in the selection screen, and further performs an operation of starting display of the V zone item, a display screen of the V zone item is displayed on the display section 25.

Figure 26:
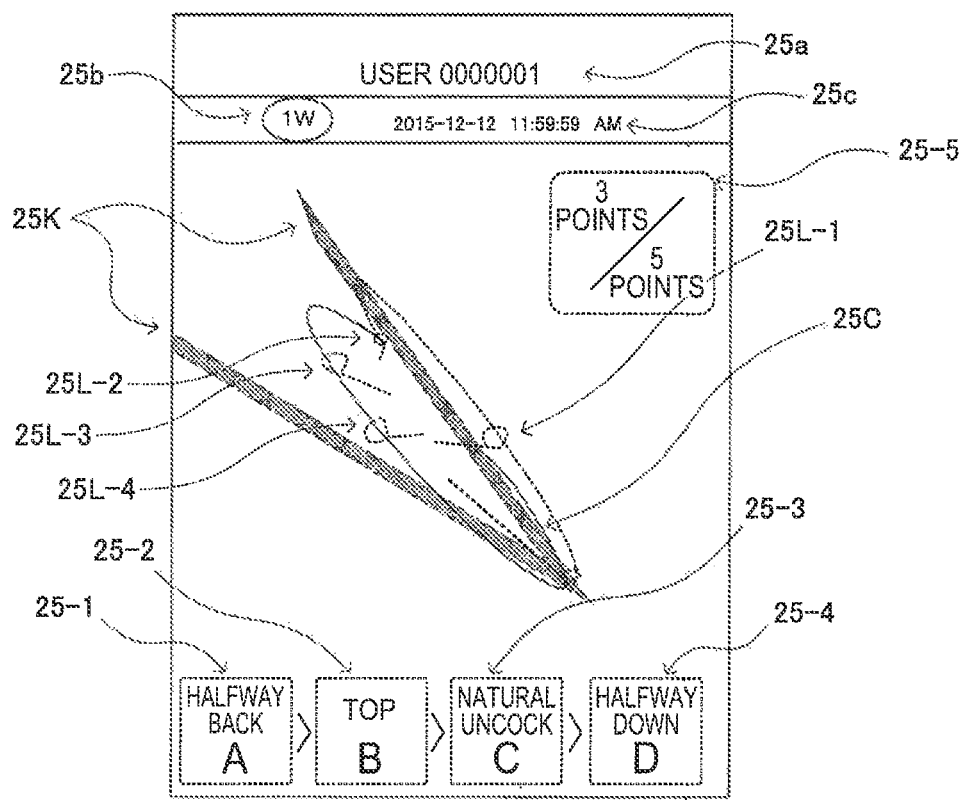
FIG. 26 is a diagram illustrating an example of a display screen of a V zone item.

FIG. 26 is a diagram illustrating an example of a display screen of the V zone item. As illustrated in FIG. 26, a text image 25a indicating an ID of the user 2, a text image 25b indicating a number of the used golf club 3 (an example of an exercise appliance), and a text image 25c indicating the date and time of a swing are disposed on an upper end part in the display screen of the V zone item.

A first display portion 25-1, a second display portion 25-2, a third display portion 25-3, and a fourth display portion 25-4 are arranged in a horizontal direction, for example, on a lower end part in the display screen of the V zone item. All of the first display portion 25-1, the second display portion 25-2, the third display portion 25-3, and the fourth display portion 25-4 indicate region arrangement patterns for a swing selected by the user 2.

In FIG. 26, an arrangement location of the four display portions 25-1, 25-2, 25-3 and 25-4 is the lower end part in the display screen, and an arrangement direction of the four display portions 25-1, 25-2, 25-3 and 25-4 is the horizontal direction of the display screen, but an arrangement location may be the upper end part or the central part in the display screen, and an arrangement direction may be the horizontal direction of the display screen; and an arrangement location may be a right end part, a left end part, or the central part, and an arrangement direction may be a vertical direction of the display screen.

Meanwhile, the first display portion 25-1 is added with a text image (in FIG. 26, "halfway back") indicating a time point (first time point) which arrives first of the time points $t_{HWB}$, $t_{top}$, $t_{vmax}$, and $t_{HWD}$, and a sign image (in FIG. 26, "A") indicating a region in which a head position is included at this time (a sign is an example of identification image). The first display portion 25-1 is added with a button function (a function of an HWB button) for notifying the user 2 of a head position at the first time point (the function of the HWB button will be described later).

Meanwhile, the second display portion 25-2 is added with a text image (in FIG. 26, "top") indicating a time point (second time point) which arrives second of the time points $t_{HWB}$, $t_{top}$, $t_{vmax}$, and $t_{HWD}$, and a sign image (in FIG. 26, "B") indicating a region in which a head position is included at this time. The second display portion 25-2 is added with a button function (a function of a top button) for notifying the user 2 of a head position at the second time point (the function of the top button will be described later).

Meanwhile, the third display portion 25-3 is added with a text image (in FIG. 26, "natural uncock") indicating a time point (third time point) which arrives third of the time points $t_{HWB}$, $t_{top}$, $t_{vmax}$, and $t_{HWD}$, and a sign image (in FIG. 26, "C") indicating a region in which a head position is included at this time. The third display portion 25-3 is added with a button function (a function of an NU button) for notifying the user 2 of a head position at the third time point (the function of the NU button will be described later).

The fourth display portion 25-4 is added with a text image (in FIG. 26, "halfway down") indicating a time point (fourth time point) which arrives fourth of the time points $t_{HWB}$, $t_{top}$, $t_{vmax}$, and $t_{HWD}$, and a sign image (in FIG. 26, "D") indicating a region in which a head position is included at this time. The fourth display portion 25-4 is added with a button function (a function of an HWD button) for notifying the user 2 of a head position at the fourth time point (the function of the HWD button will be described later).

Therefore, the user 2 can recognize a region arrangement pattern (that is, transition of regions through which the head passes during a swing) on the basis of arrangement of signs added to all of the display portions 25-1, 25-2, 25-3 and 25-4. In the example illustrated in FIG. 26, the user 2 can recognize that a region arrangement pattern is "A-B-C-D".

The user 2 may compare a region arrangement pattern for a swing when the user's condition is favorable with a region arrangement pattern for a swing when the user's condition is unfavorable, and may thus recognize the time at which a cause of the unfavorable condition is present during a swing on the basis of a difference between both of the arrangement patterns. For example, in a case where a region arrangement pattern for a swing when the condition is favorable is "C-C-C-C", and a region arrangement pattern for a swing when the condition is unfavorable is "C-C-B-C", it can be estimated that a cause of the unfavorable condition is present at an attitude of the golf club 3 at the third time point (grip deceleration start time point).

As illustrated in FIG. 26, not only the display portions 25-1, 25-2, 25-3 and 25-4, but also an image 25C of a swing trajectory (a head trajectory in FIG. 26), an image 25K of the V zone, an image 25L-1 of the golf club at the first time point, an image 25L-2 of the golf club at the second time point, an image 25L-3 of the golf club at the third time point, an image 25L-4 of the golf club at the fourth time point, and a score display portion 25-5 are disposed on the display screen of the V zone item. The image of the golf club at each time point is created on the basis of a position of the grip at each time point, a position of the head at the time point, an attitude of the sensor unit 10 at each time point, and the like. In FIG. 26, a trajectory of the head during a backswing is indicated by a dotted curved line, and a trajectory of the head during a downswing is indicated by a solid line (this is also the same for other drawings).

Above all, the score display portion 25-5 is added with a text image (in FIG. 26, "3 points/5 points") indicating a score of the V zone item. The denominator "5 points" in "3 points/5 points" indicates the highest score (maximum). The score display portion 25-5 is added with a button function (a function of a score button) for notifying the user 2 of diagnosis result of the V zone item (the function of the score button will be described later).

The user 2 checks a region arrangement pattern (in FIG. 26, "A-B-C-D") for the user's swing from the display screen of the V zone item. In a case where an attitude of the golf club 3 at the first time point is desired to be checked, the user 2 may tap the first display portion 25-1 (here, the HWB button) with the fingertip. In a case where an attitude of the golf club 3 at the second time point is desired to be checked, the user 2 may tap the second display portion 25-2 (here, the top button) with the fingertip. In a case where an attitude of the golf club 3 at the third time point is desired to be checked, the user 2 may tap the third display portion 25-3 (here, the NU button) with the fingertip. In a case where an attitude of the golf club 3 at the fourth time point is desired to be checked, the user 2 may tap the fourth display portion 25-4 (here, the HWD button) with the fingertip. In a case where a diagnosis result of the V zone item is desired to be checked, the user 2 may tap the score display portion 25-5 (score button) with the fingertip.

Figure 27:
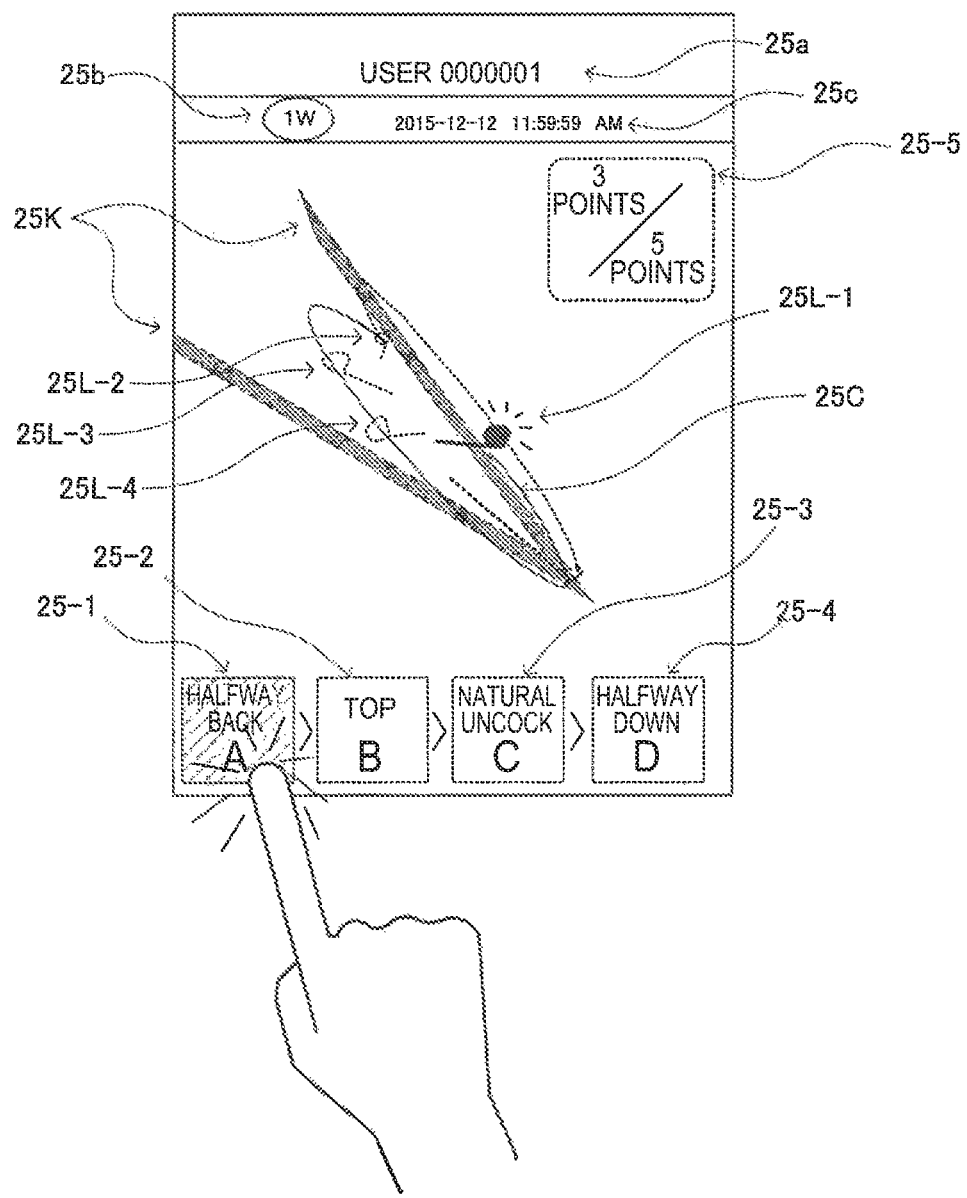
FIG. 27 is a diagram illustrating an example of a screen displayed when a first display portion (here, an HWB button) is tapped.

FIG. 27 illustrates an example of a screen displayed when the first display portion 25-1 (here, the HWB button) is tapped. As illustrated in FIG. 27, if the first display portion 25-1 (here, the HWB button) is tapped, the first display portion 25-1 (here, the HWB button) is brought into a selection state (in FIG. 27, the selection state is represented by a solid line range and is hatched), and the image 25L-1 of the golf club at the first time point is more highlighted than the images 25L-2, 25L-3 and 25L-4 of the golf club at the other time points. In the example illustrated in FIG. 27, the emphasized image 25L-1 is displayed with a relatively high contrast (thick solid line), and the images 25L-2 to 25L-4 which are not emphasized are displayed with a relatively low contrast (thin dotted line).

Figure 28:
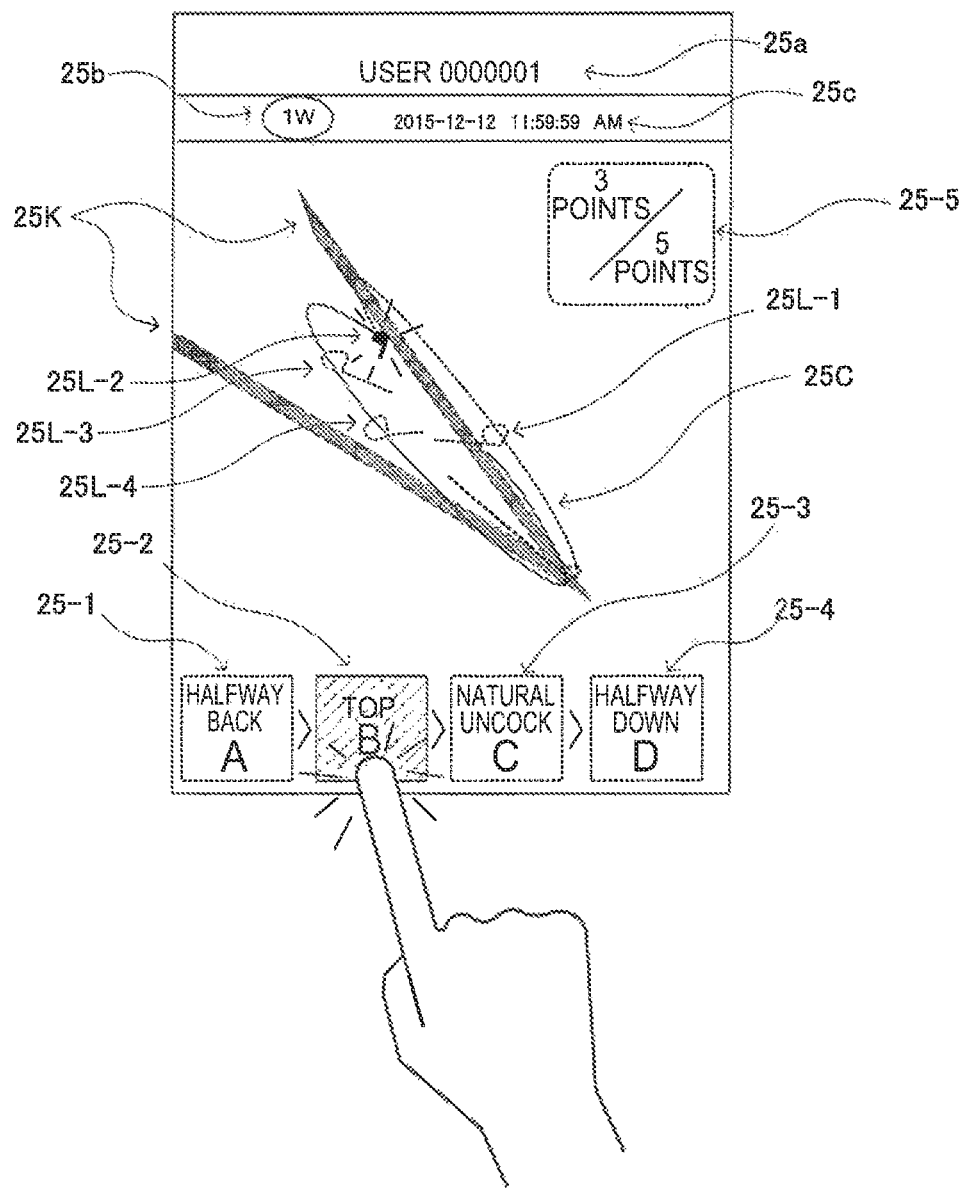
FIG. 28 is a diagram illustrating an example of a screen displayed when a second display portion (here, a top button) is tapped.

FIG. 28 illustrates an example of a screen displayed when the second display portion 25-2 (here, the top button) is tapped. As illustrated in FIG. 28, if the second display portion 25-2 (here, the top button) is tapped, the second display portion 25-2 (here, the top button) is brought into a selection state (in FIG. 28, the selection state is represented by a solid line range and is hatched), and the image 25L-2 of the golf club at the second time point is more highlighted than the images 25L-1, 25L-3 and 25L-4 of the golf club at the other time points. In the example illustrated in FIG. 28, the emphasized image 25L-2 is displayed with a relatively high contrast (thick solid line), and the images 25L-1, 25L-3 and 25L-4 which are not emphasized are displayed with a relatively low contrast (thin dotted line).

Figure 29:
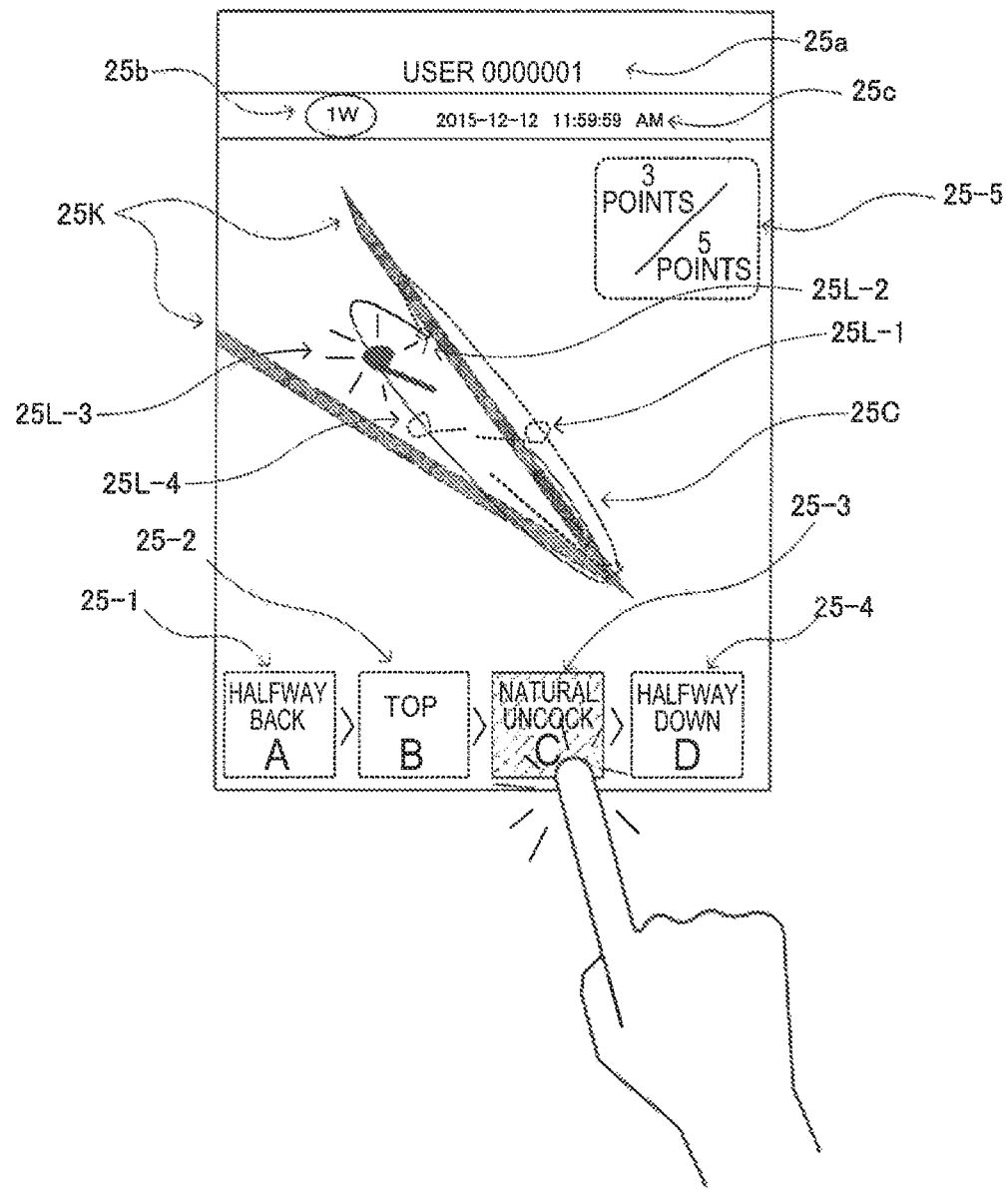
FIG. 29 is a diagram illustrating an example of a screen displayed when a third display portion (here, a NU button) is tapped.

FIG. 29 illustrates an example of a screen displayed when the third display portion 25-3 (here, the NU button) is tapped. As illustrated in FIG. 29, if the third display portion 25-3 (here, the NU button) is tapped, the third display portion 25-3 (here, the NU button) is brought into a selection state (in FIG. 29, the selection state is represented by a solid line range and is hatched), and the image 25L-3 of the golf club at the third time point is more highlighted than the images 25L-1, 25L-2 and 25L-4 of the golf club at the other time points. In the example illustrated in FIG. 29, the emphasized image 25L-3 is displayed with a relatively high contrast (thick solid line), and the images 25L-1, 25L-2 and 25L-4 which are not emphasized are displayed with a relatively low contrast (thin dotted line).

Figure 30:
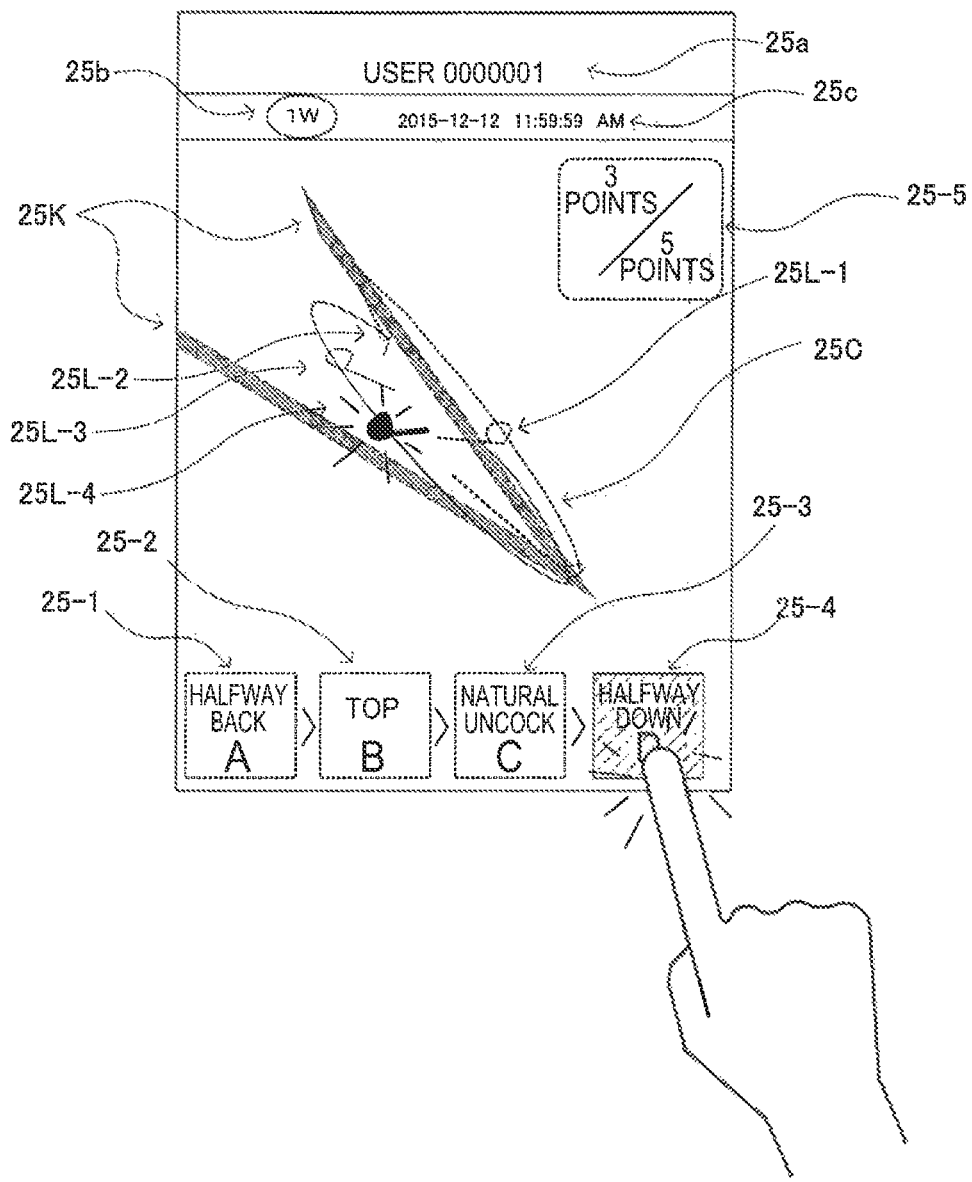
FIG. 30 is a diagram illustrating an example of a screen displayed when a fourth display portion (here, an HWD button) is tapped.

FIG. 30 illustrates an example of a screen displayed when the fourth display portion 25-4 (here, the HWB button) is tapped. As illustrated in FIG. 30, if the fourth display portion 25-4 (here, the HWD button) is tapped, the fourth display portion 25-4 (here, the HWD button) is brought into a selection state (in FIG. 30, the selection state is represented by a solid line range and is hatched), and the image 25L-4 of the golf club at the fourth time point is more highlighted than the images 25L-1, 25L-2 and 25L-3 of the golf club at the other time points. In the example illustrated in FIG. 30, the emphasized image 25L-4 is displayed with a relatively high contrast (thick solid line), and the images 25L-1, 25L-2 and 25L-3 which are not emphasized are displayed with a relatively low contrast (thin dotted line).

Figure 31:
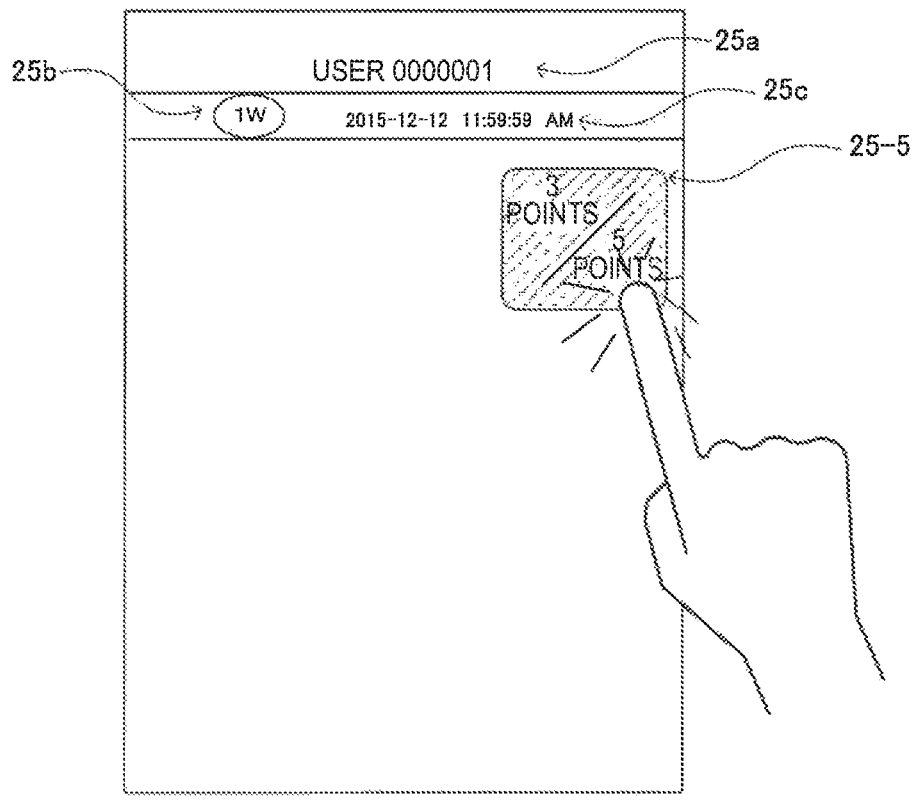
FIG. 31 is a diagram illustrating an example of a screen displayed when a score display portion (score button) is tapped.
Figure 32:
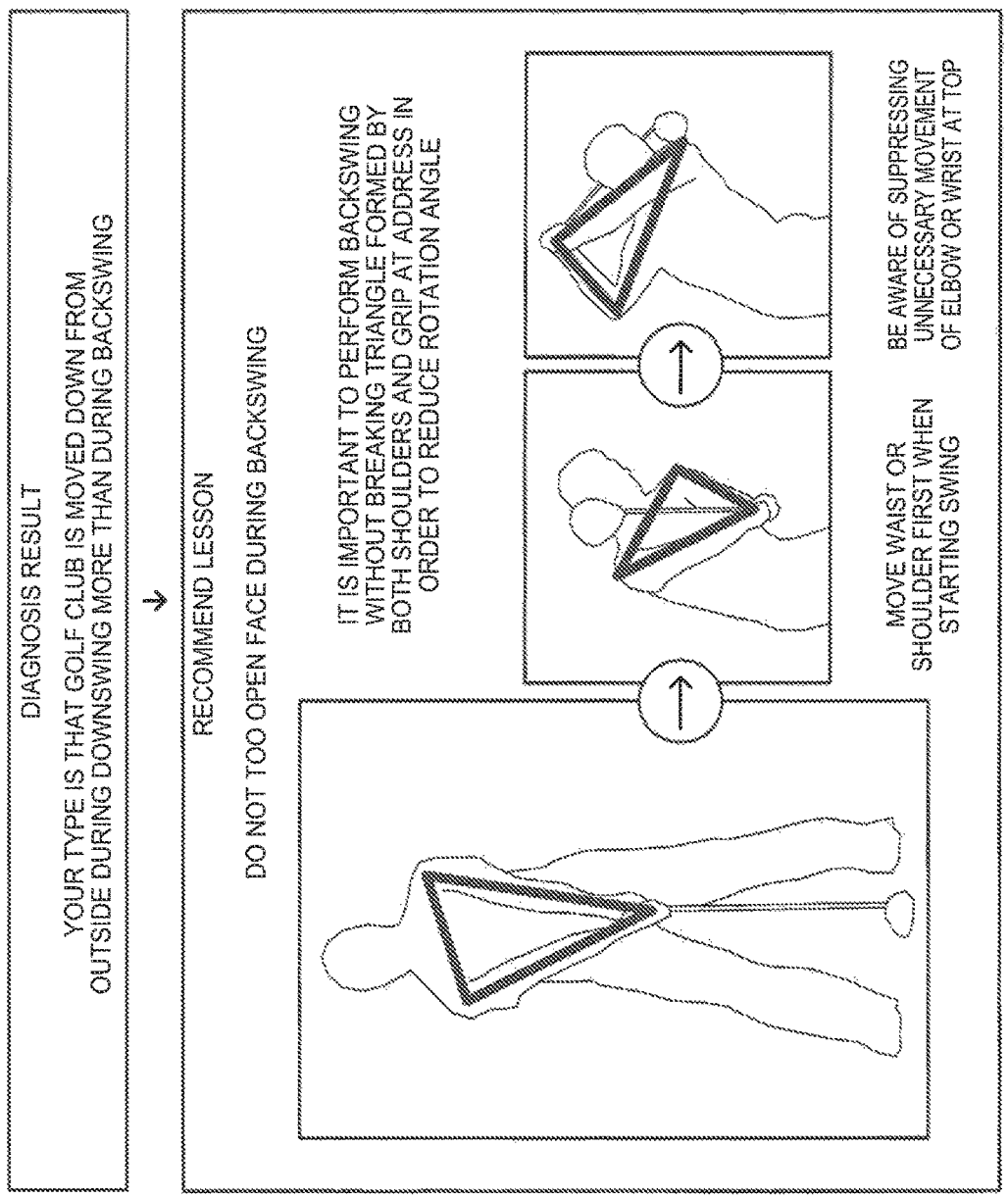
FIG. 32 is a diagram illustrating an example of a diagnosis screen for the V zone item.

As illustrated in FIG. 31, if the score display portion 25-5 (score button) is tapped, the display screen of the V zone item is replaced with, for example, a diagnosis screen of the V zone item as illustrated in FIG. 32.

As illustrated in FIG. 32, the diagnosis screen of the V zone item includes various images indicating diagnosis information of the V zone item. However, the diagnosis information illustrated in FIG. 32 is only an example, and cannot be said to correspond to the arrangement pattern ("A-B-C-D") illustrated in FIG. 26 or the like.

The diagnosis screen illustrated in FIG. 32 includes information (diagnosis result) indicating the type of swing, and one or a plurality of pieces of advice (recommended lesson) suitable for improving (overcoming) a weak point in this type of swing. A lesson method is represented by, for example, a combination of text and a still image. FIG. 32 illustrates an example in which the lesson method (advice) is represented (notified or provided) by a combination of text and a still image, but representation aspects other than the text or the still image, such as an icon, a moving image, and a voice may be used instead of the combination, and a single representation aspect or a combination of three or more representation aspects may be used.

1-6-4. Flow of V Zone Item Display Process

Hereinafter, a detailed description will be made of a flow of a V zone item display process.

In the present embodiment, if the user 2 checks any one of the checkboxes so as to select swing analysis data regarding a single swing on the selection screen illustrated in FIG. 7, then presses the OK button (taps the button with the fingertip) located on the lower part in the selection screen, and further performs an operation of starting display of the V zone item, the swing analysis apparatus 20 starts the V zone item display process.

Figure 33:
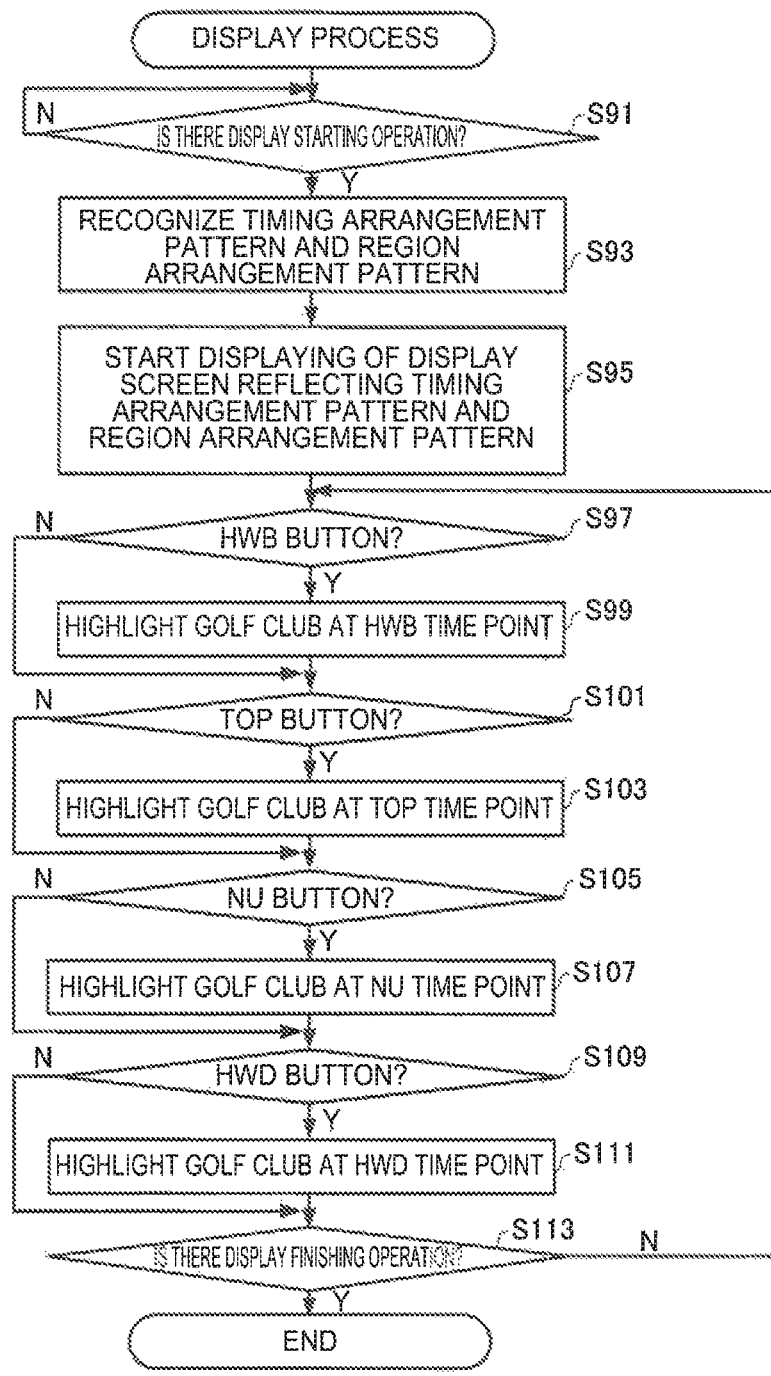
FIG. 33 is a flowchart illustrating examples of procedures of a V zone item display process performed by a processing section of a swing analysis apparatus.

FIG. 33 is a flowchart illustrating examples of procedures of the V zone item display process (an example of a presentation method) performed by the processing section 21 (an example of a presentation unit) of the swing analysis apparatus 20.

The flow in FIG. 33 represents a display process regarding the secondary screens illustrated in FIGS. 25 to 30, and does not represent a display process regarding the diagnosis screen (FIG. 32). The following process is mainly performed by the processing section 21 in cooperation between the display processing portion 214 (an example of a presentation unit) and the display section 25 (an example of a presentation unit), but will be described assuming that the processing section 21 performs the process alone. A program (an example of a presentation program) causing the processing section 21 to perform a display process is stored in the above-described storage section 24. This program may be stored in a nonvolatile recording medium (computer readable recording medium) in advance, and may be received by the processing section 21 from a server (not illustrated) or the server apparatus 30 via a network so as to be stored in the storage section 24.

First, the processing section 21 determines whether or not there is an operation of starting display of the V zone item, proceeds to the next process (step S93) if there is the display starting operation (Y in step S91), and waits if there is no display starting operation (N in step S91).

Next, the processing section 21 recognizes a timing arrangement pattern and a region arrangement pattern included in swing analysis data selected by the user 2 (step S93). Here, it is assumed that the timing arrangement pattern is "$t_{HWB}$-$t_{top}$-$t_{vmax}$-$t_{HWD}$", and the region arrangement pattern is "A-B-C-D".

Next, the processing section 21 starts to display a display screen reflecting the timing arrangement pattern "$t_{HWB}$-$t_{top}$-$t_{vmax}$-$t_{HWD}$" and the region arrangement pattern "A-B-C-D" (step S95). Here, since a timing arrangement pattern is "$t_{HWB}$-$t_{top}$-$t_{vmax}$-$t_{HWD}$", on the display screen, the first display portion 25-1 is added with a function of the HWB button, the second display portion 25-2 is added with a function of the top button, the third display portion 25-3 is added with a function of the NU button, and the fourth display portion 25-4 is added with a function of the HWD button. Images at the four time points are also disposed on the display screen.

Next, when the display screen is displayed, the processing section 21 performs a process of determining whether or not the first display portion 25-1 (here, the HWB button) has been tapped (step S97), a process of determining whether or not the second display portion 25-2 (here, the top button) has been tapped (step S101), a process of determining whether or not the third display portion 25-3 (here, the NU button) has been tapped (step S105), a process of determining whether or not the fourth display portion 25-4 (here, the HWD button) has been tapped (step S109), and a process of determining whether or not an operation of finishing display of the V zone item has been performed (step S113), and repeatedly performs the determination processes (steps S97, S101, S105, S109 and S113) unless the operation of finishing display of the V zone item is performed (N in step S113).

Then, if the first display portion 25-1 (here, the HWB button) is tapped (Y in step S97), the processing section 21 starts to highlight the image of the golf club at the first time point (here, the halfway back time point) (step S99).

Then, if the second display portion 25-2 (here, the top button) is tapped (Y in step S101), the processing section 21 starts to highlight the image of the golf club at the second time point (here, the top time point) (step S103).

Then, if the third display portion 25-3 (here, the NU button) is tapped (Y in step S105), the processing section 21 starts to highlight the image of the golf club at the third time point (here, the grip deceleration start time point) (step S107).

Then, if the fourth display portion 25-4 (here, the HWD button) is tapped (Y in step S109), the processing section 21 starts to highlight the image of the golf club at the fourth time point (here, the halfway down time point).

If there is an operation of finishing the display of the V zone item (Y in step S113), the processing section 21 finishes the flow at that time.

In the flowchart of FIG. 33, order of the respective steps may be changed as appropriate within an allowable range, some of the steps may be omitted or changed, and other steps may be added thereto.

1-7. Operations and Effects

As described above, the swing analysis apparatus 20 of the present embodiment presents an identification sign indicating a region in which the head of the golf club 3 is included at each of the time points $t_{HWB}$, $t_{top}$, $t_{vmax}$ and $t_{HWD}$ of a plurality of regions A, B, C, D and E to which the identification signs A, B, C, D and E are added in advance, to the user 2 in a time series.

According to the swing analysis apparatus 20 of the present embodiment, identification signs of regions in which the head of the golf club 3 is included at the plurality of respective time points $t_{HWB}$, $t_{top}$, $t_{vmax}$ and $t_{HWD}$ are presented in a time series (that is, in order of a plurality of time points $t_{HWB}$, $t_{top}$, $t_{vmax}$ and $t_{HWD}$ arriving), and thus the user 2 can recognize the type of user's swing as an arrangement pattern of the identification signs. Specifically, the user 2 objectively and simply can recognize the type of user's swing as any one of "A-A-A-A", "A-A-A-B", "A-A-A-C", . . . , and "E-E-E-E".

Therefore, the user 2 compares a region arrangement pattern for a swing when the user's condition is favorable with a region arrangement pattern for a swing when the user's condition is unfavorable, and can thus recognize the time at which a cause of the unfavorable condition is present during a swing on the basis of a difference between both of the arrangement patterns. For example, in a case where a region arrangement pattern for a swing when the condition is favorable is "C-C-C-C", and a region arrangement pattern for a swing when the condition is unfavorable is "C-C-B-C", it can be estimated that a cause of the unfavorable condition is present at an attitude of the golf club 3 at the third time point (grip deceleration start time point).

2. Modification Examples

The invention is not limited to the present embodiment, and may be variously modified within the scope of the spirit of the invention.

2-1. Other Presentation Aspects

In the above-described embodiment, the processing section 21 arranges the identification signs (A, B, C, D, and E) of the respective regions in a spatial direction in order to a region arrangement pattern to the user 2, but may arrange the identification signs (A, B, C, D, and E) of the respective regions in a temporal direction. In other words, in order to present an arrangement pattern "A-B-C-D" to the user 2, the processing section 21 in the above-described embodiment may sequentially display an image indicating the sign "A", an image indicating the sign "B", an image indicating the sign "C", and an image indicating the sign "D" on a screen, and may output a sound indicating the sign "A", a sound indicating the sign "B", a sound indicating the sign "C", and a sound indicating the sign "D". The outputting of a voice is performed in cooperation between the sound output processing portion 215 of the processing section 21 and the sound output section 26.

In the above-described embodiment, the processing section 21 uses identification signs such as "A", "B", "C", "D", and "E", as identification data of the regions, but may use identification numbers such as "1", "2", "3", "4", and "5", may use identification words such as "upper side of V zone", "Hogan plane side in V zone", "center of V zone", "shaft plane side of V zone", and "lower side of V zone", and may use identification words such as "upper side of standard range", "upper side in standard range", "lower side in standard range", and "lower side of standard range".

2-2. Other Notification Aspects

In the above-described embodiment, the processing section 21 mainly performs a single or a plurality of notifications for the user 2 on the screen, but may perform a notification according to other aspects. As a notification aspect, for example, at least one of an image, light, sound, vibration, an image change pattern, a light change pattern, a sound change pattern, and a vibration change pattern may be used.

2-3. Other Input Aspects

In the above-described embodiment, the processing section 21 mainly inputs a single or a plurality of pieces of information from the user 2 through touching of the finger (a tapping operation on a touch panel or an operation on a button), but various aspects may be used as an aspect of inputting a single or a plurality of pieces of information. As an aspect of inputting information, for example, at least one of information input through touching of the finger, information input using a voice, and information input using gesture.

2-4. Modification of V Zone

Figure 34:
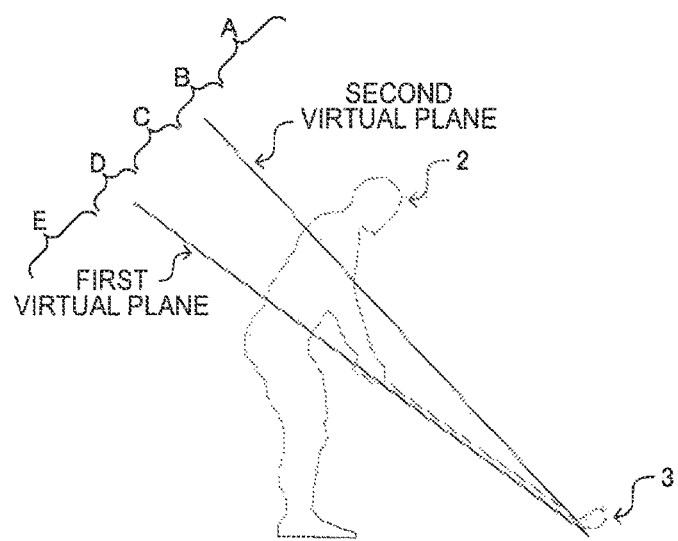
FIG. 34 is a diagram for explaining a V zone (a first virtual plane and a second virtual plane).
Figure 35:
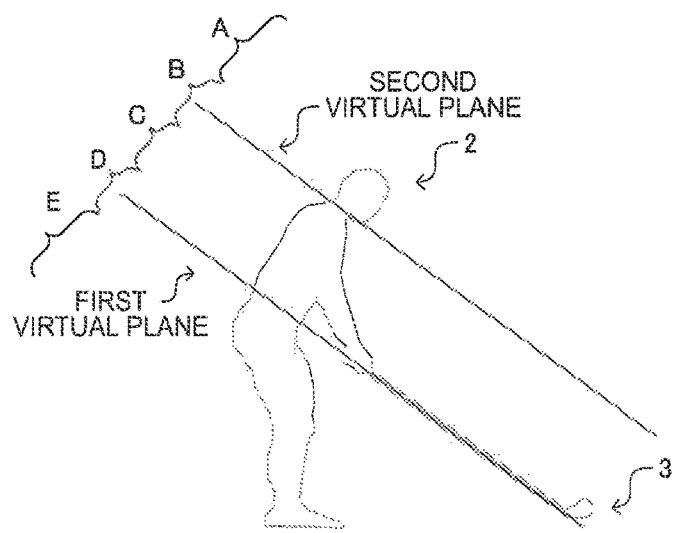
FIG. 35 is a diagram illustrating a modification example of the first virtual plane and the second virtual plane.

In the above-described embodiment, the concept of the V zone (a region interposed between the shaft plane and the Hogan plane) is introduced in order to define the regions A, B, C, D and E in which the head is included. The V zone is a region interposed between the first virtual plane along the longitudinal direction of the golf club 3 and the second virtual plane passing through the vicinity of the shoulder of the user 2 (refer to FIG. 34). The first virtual plane is, for example, a so-called shaft plane specified by a first axis along a target hit ball direction and a second axis along the longitudinal direction of the golf club 3 before a swing is started. The second virtual plane is, for example, a so-called Hogan plane which includes the first axis, and forms a predetermined angle with the first virtual plane. However, the second virtual plane may be a virtual plane (including both of a virtual plane parallel to the first virtual plane and a virtual plane along the first virtual plane) which is parallel to the first virtual plane. A parallel virtual plane may be referred to as a "shoulder plane" (refer to FIG. 35). In the above-described embodiment, the second virtual plane may be calculated on the basis of both of the first virtual plane and physical information of the user 2, and a plane having a predetermined relationship with the first virtual plane may be the second virtual plane.

Figure 36:
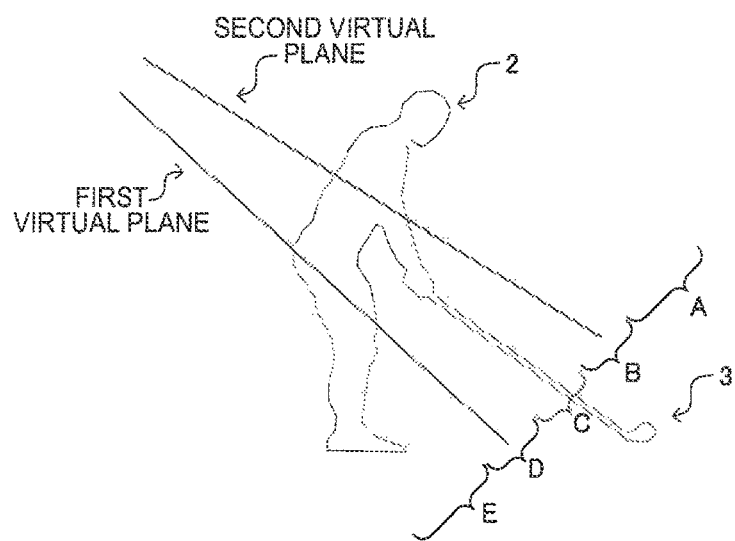
FIG. 36 is a diagram illustrating another modification example of the first virtual plane and the second virtual plane.

A method of defining the first virtual plane and the second virtual plane is not limited thereto, and, for example, virtual planes as illustrated in FIG. 36 may be used. Two virtual planes illustrated in FIG. 36 are virtual planes which are set on the basis of an attitude of the shaft before a swing is started, in which a first plane is a virtual plane passing through the vicinity of the elbow of the user 2, and a second plane is a virtual plane passing through the vicinity of the knee of the user. The first virtual plane and the second virtual plane are not parallel to each other, and intersect each other on a straight line extending in a grip end direction of the golf club, for example.

2-5. Modifications of Swing Analysis Process

For example, a plurality of sensor units 10 may be attached to the golf club 3 or parts such as the arms or the shoulders of the user 2, and the swing analysis portion 211 may perform a swing analysis process by using measured data from the plurality of sensor units 10.

In the embodiment, the swing analysis portion 211 calculates the third line segment 53 which is a third axis and the Hogan plane HP by using the physical information of the user 2, but a line segment and a plane obtained by rotating the second line segment 52 which is a second axis and the shaft plane SP by a predetermined first angle $\beta$ (for example, 30°) about the X axis, respectively, may be used as the third line segment 53 and the Hogan plane HP.

In the embodiment, the swing analysis portion 211 detects impact by using the square root of the square sum as shown in Equation (2) as a combined value of three-axis angular velocities measured by the sensor unit, but, as a combined value of three-axis angular velocities, for example, a square sum of three-axis angular velocities, a sum or an average of three-axis angular velocities, or the product of three-axis angular velocities may be used. Instead of a combined value of three-axis angular velocities, a combined value of three-axis accelerations such as a square sum or a square root of three-axis accelerations, a sum or an average value of three-axis accelerations, or the product of three-axis accelerations may be used.

2-6. Modification Examples Such as HMD

Figure 37:
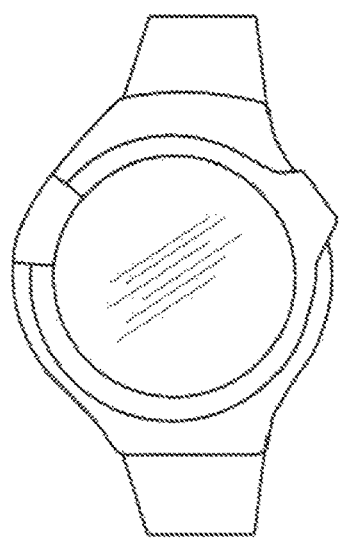
FIG. 37 is a diagram illustrating an example of a wrist type display section.
Figure 38:
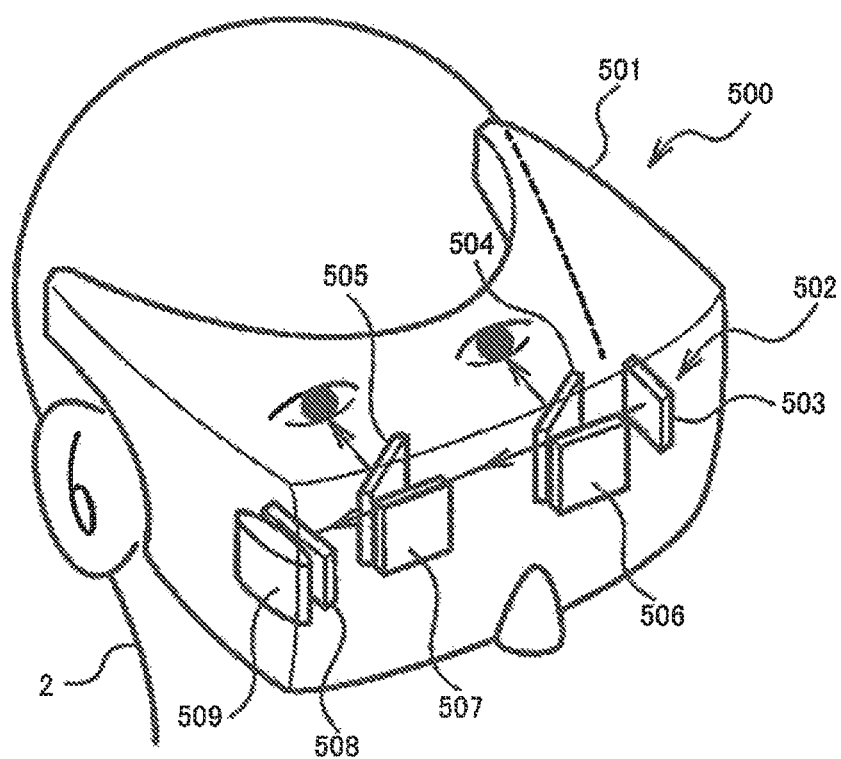
FIG. 38 is a diagram illustrating an example of a head mounted display.

In the above-described embodiment, as a display location of a single or a plurality of images, for example, a wrist type display section (an example of a wrist mounted display device) as illustrated in FIG. 37 or a head mounted display section (hereinafter, referred to as an HMD; an example of a head mounted display device) as illustrated in FIG. 38 may be used.

The head mounted display is a display which is mounted on the head of the user 2, and displays an image with respect to one eye or both eyes of the user 2. The user 2 wearing the head mounted display on the head thereof can recognize various images without deviating a visual line thereof from the head of the golf club 3, or a target direction.

As illustrated in FIG. 38, an HMD 500 includes a spectacle main body 501 mounted on the head of the user 2. The spectacle main body 501 is provided with a display section 502. The display section 502 integrates a light beam emitted from an image display unit 503 with a light beam directed toward the eyes of the user 2, and thus overlaps a virtual image on the image display unit 503 with a real image of the external world viewed from the user 2.

The display section 502 is provided with, for example, the image display unit 503 such as an liquid crystal display (LCD), a first beam splitter 504, a second beam splitter 505, a first concave reflection mirror 506, a second concave reflection mirror 507, a shutter 508, and a convex lens 509.

The first beam splitter 504 is disposed on the front side of the left eye of the user 2, and partially transmits and partially reflects light emitted from the image display unit 503.

The second beam splitter 505 is disposed on the front side of the right eye of the user 2, and partially transmits and partially reflects light which is partially transmitted from the first beam splitter 504.

The first concave reflection mirror 506, which is disposed in front of the first beam splitter 504, partially reflects the partially reflected light from the first beam splitter 504 so as to transmit the light through the first beam splitter 504, and thus guides the light to the left eye of the user 2.

The second concave reflection mirror 507, which is disposed in front of the second beam splitter 505, partially reflects the partially reflected light from the second beam splitter 505 so as to transmit the light through the second beam splitter 505, and thus guides the light to the right eye of the user 2.

The convex lens 509 guides partially transmitted light from the second beam splitter 505 to the outside of the HMD 500 when the shutter 508 is opened.

According to the HMD 500, the user 2 can understand necessary information without holding the swing analysis apparatus 20 with the hands.

2-7. Others

In the above-described embodiment, some or all of the functions of the sensor unit 10 may be installed on the swing analysis apparatus 20 side or the server apparatus 30 side. Some or all of the functions of the swing analysis apparatus 20 may be installed on the sensor unit 10 side or the server apparatus 30 side. Some or all of the functions of the server apparatus 30 may be installed on the swing analysis apparatus 20 side or the sensor unit 10 side.

In the embodiment, the acceleration sensor 12 and the angular velocity sensor 14 are built into and are thus integrally formed as the sensor unit 10, but the acceleration sensor 12 and the angular velocity sensor 14 may not be integrally formed. Alternatively, the acceleration sensor 12 and the angular velocity sensor 14 may not be built into the sensor unit 10, and may be directly mounted on the golf club 3 or the user 2. In the above-described embodiment, the sensor unit 10 and the swing analysis apparatus 20 are separately provided, but may be integrally formed so as to be attached to the golf club 3 or the user 2. The sensor unit 10 may have some of the constituent elements of the swing analysis apparatus 20 along with the inertial sensor (for example, the acceleration sensor 12 or the angular velocity sensor 14).

The inertial sensor may be a sensor which can measure an inertial amount such as acceleration or angular velocity, and may be, for example, an inertial measurement unit (IMU) which can measure acceleration or angular velocity. For example, the inertial sensor may be attached to an exercise appliance or a part of a user so as to be attachable to and detachable from the exercise appliance or the user, and may be fixed to the exercise appliance so as to not be detached therefrom as a result of being built into the exercise appliance.

In the above-described embodiment, the swing analysis system (server apparatus) analyzing a golf swing has been exemplified, but the invention is applicable to a swing analysis system (server apparatus) analyzing a swing in various sports such as tennis or baseball.

The above-described embodiment and modification examples are only examples, and the invention is not limited thereto. For example, the embodiment and the respective modification examples may be combined with each other as appropriate.

For example, the invention includes substantially the same configuration (for example, a configuration in which functions, methods, and results are the same, or a configuration in which objects and effects are the same) as the configuration described in the embodiment. The invention includes a configuration in which an inessential part of the configuration described in the embodiment is replaced with another part. The invention includes a configuration which achieves the same operation and effect or a configuration capable of achieving the same object as in the configuration described in the embodiment. The invention includes a configuration in which a well-known technique is added to the configuration described in the embodiment.

What is claimed is:

1. An electronic apparatus comprising:
   a processor configured to determine identification data indicating a region in which a ball hitting portion of an exercise appliance is included at each of a plurality of timings during a swing of the exercise appliance, of a plurality of regions to which the identification data is allocated, based on an output from an inertial sensor disposed on the exercise appliance or on a user, the plurality of regions including:
   a first region including a first virtual plane formed from a line extending along a central axis of a shaft of the exercise appliance at an initial position prior to a start of a backswing of the exercise appliance;
   a second region including a second virtual plane formed from a line calculated based on a location of one end of the shaft and a location identified by inputted physical information, at the start of the backswing of the exercise appliance; and
   a third region disposed between the first region and the second region; and
   a display configured to display the identification data indicating the region in which the ball hitting portion of the exercise appliance is included at each of the plurality of timings during the swing of the exercise appliance.

2. The electronic apparatus according to claim 1, wherein the processor is configured to determine the identification data in a time series according to a swing action of the exercise appliance for presentation on the display.

3. The electronic apparatus according to claim 1, wherein the plurality of regions are set based on the first virtual plane indicating a basic attitude of the exercise appliance.

4. The electronic apparatus according to claim 1, wherein the first virtual plane is a plane specified based on a first axis along a target hit ball direction and a second axis along a longitudinal direction of the shaft of the exercise appliance before the backswing is started.

5. The electronic apparatus according to claim 4, wherein the plurality of regions are set based on the first virtual plane and the second virtual plane, the second virtual plane including the first axis and forming a predetermined angle with the first virtual plane.

6. The electronic apparatus according to claim 5, wherein the second virtual plane passes through a vicinity of a shoulder of the user.

7. The electronic apparatus according to claim 5, wherein the processor outputs data specifying the first virtual plane and the second virtual plane for display along with the identification data.

8. The electronic apparatus according to claim 4, wherein the plurality of regions are set based on the first virtual plane and the second virtual plane, the second virtual plane being parallel to the first virtual plane.

9. The electronic apparatus according to claim 1, wherein the processor outputs data specifying a trajectory of the swing for display along with the identification data.

10. The electronic apparatus according to claim 1, wherein the plurality of timings include at least two timings at which a longitudinal direction of the shaft of the exercise appliance is along a horizontal plane during the backswing, a timing of a top of the swing, a timing at which a holding portion of the exercise appliance starts to decelerate during a downswing, and a timing at which the longitudinal direction of the shaft of the exercise appliance is along the horizontal plane during the downswing.

11. The electronic apparatus according to claim 1, wherein the inertial sensor includes at least one of an acceleration sensor and an angular velocity sensor.

12. The electronic apparatus according to claim 1, wherein the processor is configured to calculate a level based on the presented identification data for display to the user.

13. The electronic apparatus according to claim 1, wherein the processor is configured to calculate diagnosis information based on the determined identification data.

14. The electronic apparatus according to claim 13, wherein the processor is configured to present information regarding a swing practice method based on the diagnosis information.

15. The electronic apparatus according to claim 1, wherein the display is a head mounted display device.

16. The electronic apparatus according to claim 1, wherein the display is a wrist mounted display device.

17. A system comprising:
the electronic apparatus according to claim 1; and
the inertial sensor.

18. A presentation method comprising:
determining identification data indicating a region in which a ball hitting portion of an exercise appliance is included at each of a plurality of timings during a swing of the exercise appliance, of a plurality of regions to which the identification data is allocated, based on an output from an inertial sensor disposed on the exercise appliance or on a user, the plurality of regions including:
a first region including a first virtual plane formed from a line extending along a central axis of a shaft of the exercise appliance at an initial position prior to a start of a backswing of the exercise appliance;
a second region including a second virtual plane formed from a line calculated based on a location of one end of the shaft and a location identified by inputted physical information, at the start of the backswing of the exercise appliance; and
a third region disposed between the first region and the second region; and
displaying the identification data indicating the region in which the ball hitting portion of the exercise appliance is included a each of the plurality of timings during the swing of the exercise appliance.

19. The presentation method according to claim 18, wherein, the identification data is displayed to the user in a time series according to a swing action.

20. The presentation method according to claim 18, wherein the plurality of regions are set based on the first virtual plane indicating a basic attitude of the exercise appliance.

21. The presentation method according to claim 20, wherein the first virtual plane is specified based on first axis along a target hit ball direction and a second axis along a longitudinal direction of the shaft of the exercise appliance before the backswing of the exercise appliance is started.

22. The presentation method according to claim 21, wherein the plurality of regions are set based on the first virtual plane and the second virtual plane, the second virtual plane including the first axis and forming a predetermined angle with the first virtual plane.

23. The presentation method according to claim 22, wherein the second virtual plane passes through a vicinity of a shoulder of the user.

24. The presentation method according to claim 22, wherein, in the display of the identification data, the first virtual plane and the second virtual plane are displayed along with the identification data.

25. The presentation method according to claim 21, wherein the plurality of regions are set based on of the first virtual plane and the second virtual plane, the second virtual plane being parallel to the first virtual plane.

26. The presentation method according to claim 18, wherein, in the display of the identification data, a trajectory of the swing is displayed along with the identification data.

27. The presentation method according to claim 18, wherein the plurality of timings include at least two timings at which a longitudinal direction of the shaft of the exercise appliance is along a horizontal plane during the backswing, a timing of a top of the swing, a timing at which a holding portion of the exercise appliance starts to decelerate during a downswing, and a timing at which the longitudinal direction of the shaft of the exercise appliance is along the horizontal plane during the downswing.

28. A non-transitory computer-readable recording medium recording a presentation program configured to be executed by a processor of a computer to:
determine identification data indicating a region in which a ball hitting portion of an exercise appliance is included at each of a plurality of timings during a swing of the exercise appliance, of a plurality of regions to which the identification data is allocated, based on an output from an inertial sensor disposed on the exercise appliance or on a user, the plurality of regions including:
a first region including a first virtual plane formed from a line extending a long a central axis of a shaft of the exercise appliance at an initial position prior to a start of a backswing of the exercise appliance;
a second region including a second virtual plane formed from a line calculated based on a location of one end of the shaft and a location identified by inputted physical information, at the start of the backswing of the exercise appliance; and
a third region disposed between the first region and the second region; and
display the identification data indicating the region in which the ball hitting portion of the exercise appliance is included at each of the plurality of timings during the swing of the exercise appliance.

* * * * *